US012653542B2

(12) United States Patent
Roundy et al.

(10) Patent No.: US 12,653,542 B2
(45) Date of Patent: **\*Jun. 16, 2026**

(54) CLIPS AND APPLICATOR FOR TISSUE CLOSURE

(71) Applicant: Oregon Health & Science University, Portland, OR (US)

(72) Inventors: Neil Roundy, Eugene, OR (US); Rachel Dreilinger, Lake Oswego, OR (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 269 days.

This patent is subject to a terminal disclaimer.

(21) Appl. No.: 18/139,540

(22) Filed: Apr. 26, 2023

(65) Prior Publication Data

US 2023/0255636 A1 Aug. 17, 2023

Related U.S. Application Data

(63) Continuation of application No. 15/853,324, filed on Dec. 22, 2017, now Pat. No. 11,660,097, which is a
(Continued)

(51) Int. Cl.
*A61B 17/122* (2006.01)
*A61B 17/00* (2006.01)
(Continued)

(52) U.S. Cl.
CPC ........ *A61B 17/122* (2013.01); *A61B 17/1285* (2013.01); *A61B 2017/00659* (2013.01);
(Continued)

(58) Field of Classification Search
None
See application file for complete search history.

(56) References Cited

U.S. PATENT DOCUMENTS

| 3,378,010 A | 4/1968 | Codling et al. |
| 3,601,127 A | 8/1971 | Finegold |
| (Continued) | | |

FOREIGN PATENT DOCUMENTS

| BR | 112017009196 | 1/2018 |
| BR | 1120170091968 | 12/2021 |
| (Continued) | | |

OTHER PUBLICATIONS

European Patent Office; European Search Report including Supplementary European Search Report for EP15856303; Jun. 5, 2018; 8 pages.
(Continued)

*Primary Examiner* — Shaun L David
(74) *Attorney, Agent, or Firm* — LAW OFFICE OF KAREN DANA OSTER, LLC

(57) ABSTRACT

Surgical clips and surgical applicators used in performing rapid tissue closure in either minimally invasive surgeries or traditional open procedures are provided. In one example approach, a surgical clip comprises opposing sides extending from a top portion and terminating at tips positioned below the top portion. The resting position of the clip is its closed position. Edges of the top portion and the opposing sides form opposing faces perpendicular to the opposing sides. The opposing faces are angled inwardly towards each other at a region of the faces adjacent to the top portion. Grooves are formed in each of the opposing sides. The grooves are configured to engage inwardly turned tracks of a clip applicator such that, when a force is applied to the clip, the opposing sides bend outwardly away from each other to place the clip in an intermediate open position.

20 Claims, 23 Drawing Sheets

Related U.S. Application Data continuation of application No. 14/930,595, filed on Nov. 2, 2015, now Pat. No. 9,883,866.

(60) Provisional application No. 62/074,212, filed on Nov. 3, 2014.

(51) Int. Cl.
    *A61B 17/02* (2006.01)
    *A61B 17/128* (2006.01)

(52) U.S. Cl.
    CPC . *A61B 2017/00668* (2013.01); *A61B 17/0293* (2013.01); *A61B 17/1222* (2013.01)

(56) References Cited

U.S. PATENT DOCUMENTS

| | | | |
|---|---|---|---|
| 3,604,425 | A | 9/1971 | Le Roy |
| 4,187,712 | A | 2/1980 | Samuels et al. |
| 4,217,902 | A | 8/1980 | March |
| 4,478,221 | A | 10/1984 | Heiss |
| 4,505,273 | A | 3/1985 | Braun et al. |
| 4,821,721 | A | 4/1989 | Chin et al. |
| 4,938,214 | A | 7/1990 | Specht |
| 4,971,198 | A | 11/1990 | Mericle |
| 4,983,176 | A | 1/1991 | Cushman et al. |
| 5,007,921 | A | 4/1991 | Brown |
| 5,047,049 | A | 9/1991 | Salai |
| 5,065,516 | A | 11/1991 | Dulebohn |
| 5,104,397 | A | 4/1992 | Vasconcelos et al. |
| 5,192,288 | A | 3/1993 | Thompson et al. |
| 5,207,692 | A | 5/1993 | Kraus et al. |
| 5,236,436 | A | 8/1993 | Koros et al. |
| 5,366,458 | A | 11/1994 | Korthoff et al. |
| 5,405,353 | A | 4/1995 | Randall |
| 5,425,489 | A | 6/1995 | Shichman et al. |
| 5,520,704 | A | 5/1996 | Castro et al. |
| 5,591,178 | A | 1/1997 | Green et al. |
| 5,725,542 | A | 3/1998 | Yoon |
| 5,779,720 | A | 7/1998 | Walder-Utz et al. |
| 6,120,526 | A | 9/2000 | Daley |
| 6,283,984 | B1 | 9/2001 | Ray |
| 6,352,541 | B1 | 3/2002 | Kienzle et al. |
| 6,425,903 | B1 | 7/2002 | Voehele |
| 6,460,700 | B2 | 10/2002 | Weisshaupt |
| 6,537,289 | B1 | 3/2003 | Kayan et al. |
| 6,679,894 | B2 | 1/2004 | Damarati |
| 7,533,790 | B1 | 5/2009 | Knodel et al. |
| 8,075,481 | B2 | 12/2011 | Park et al. |
| 8,393,517 | B2 | 3/2013 | Milo |
| 8,398,655 | B2 | 3/2013 | Cheng et al. |
| 9,358,008 | B2 | 6/2016 | Mazzucco et al. |
| 9,883,866 | B2 | 2/2018 | Roundy et al. |
| 10,368,888 | B2 | 8/2019 | Storz et al. |
| 11,051,814 | B2 | 7/2021 | Roundy et al. |
| 2002/0111641 | A1 | 8/2002 | Peterson et al. |
| 2004/0059378 | A1 | 3/2004 | Peterson et al. |
| 2004/0087985 | A1 | 5/2004 | Loshakove et al. |
| 2004/0138705 | A1 | 7/2004 | Heino et al. |
| 2004/0138765 | A1 | 7/2004 | Bonissone et al. |
| 2005/0107807 | A1 | 5/2005 | Nakao |
| 2005/0149064 | A1 | 7/2005 | Peterson et al. |
| 2005/0216036 | A1 | 9/2005 | Nakao |
| 2007/0073314 | A1 | 3/2007 | Gadberry et al. |
| 2007/0208358 | A1 | 9/2007 | Kayan |
| 2008/0065154 | A1 | 3/2008 | Allard |
| 2008/0103510 | A1 | 5/2008 | Taylor |
| 2008/0312670 | A1 | 12/2008 | Lutze |
| 2009/0030448 | A1 | 1/2009 | Andre |
| 2009/0072006 | A1 | 3/2009 | Clauson et al. |
| 2009/0206144 | A1 | 8/2009 | Doll et al. |
| 2010/0010511 | A1 | 1/2010 | Harris et al. |
| 2010/0016875 | A1 | 1/2010 | Nakao et al. |
| 2010/0191262 | A1 | 7/2010 | Harris et al. |
| 2010/0191282 | A1 | 7/2010 | Harris et al. |
| 2010/0204717 | A1 | 8/2010 | Knodel |
| 2010/0312259 | A1 | 12/2010 | Houser et al. |
| 2011/0112551 | A1 | 5/2011 | Adams et al. |
| 2013/0172914 | A1 | 7/2013 | Weisshaupt |
| 2014/0128819 | A1 | 5/2014 | Eaves |
| 2014/0296884 | A1 | 10/2014 | Motomura |
| 2015/0080914 | A1 | 3/2015 | Roundy et al. |
| 2018/0116669 | A1 | 5/2018 | Roundy et al. |
| 2021/0322010 | A1 | 10/2021 | Roundy et al. |
| 2021/0330328 | A1 | 10/2021 | Roundy et al. |

FOREIGN PATENT DOCUMENTS

| | | |
|---|---|---|
| CA | 2133687 C | 3/2007 |
| CA | 2965986 C | 5/2019 |
| CN | 102292035 | 12/2011 |
| CN | 103989501 C | 8/2014 |
| CN | 103989501 B | 3/2016 |
| CN | 107106182 | 8/2017 |
| CN | 107106182 B | 11/2019 |
| DE | 3204532 C2 | 12/1983 |
| DE | 19752331 C1 | 9/1999 |
| DE | 102006031092 B3 | 1/2008 |
| DE | 29720952 U1 | 5/2019 |
| EP | 0159453 A1 | 6/1989 |
| EP | 0469524 A1 | 2/1992 |
| EP | 0565892 A1 | 10/1993 |
| EP | 1895917 B1 | 9/2008 |
| EP | 2701613 B1 | 9/2016 |
| EP | 3113699 B1 | 8/2017 |
| JP | S58138447 A | 8/1983 |
| JP | H057593 A | 1/1993 |
| JP | H07236644 | 9/1995 |
| JP | 3124027 B2 | 1/2001 |
| JP | 2005530559 A | 10/2005 |
| JP | 2017523810 A | 8/2017 |
| JP | 2017533042 A | 11/2017 |
| JP | 6532113 B2 | 5/2019 |
| KR | 101773205 B1 | 9/2017 |
| WO | 1990010418 A1 | 9/1990 |
| WO | 2010118312 A2 | 10/2010 |
| WO | 2011059666 A2 | 5/2011 |
| WO | 2012135735 A2 | 10/2012 |
| WO | 2015039024 A1 | 3/2015 |
| WO | 2016073376 A1 | 5/2016 |
| WO | 2021214729 A1 | 10/2021 |

OTHER PUBLICATIONS

Patent Cooperation Treaty; International Preliminary Report on Patentability and Written Opinion of PCT/US2015/058669; May 9, 2017; 6 pages.

Patent Cooperation Treaty; International Search Report and Written Opinion of the International Searching Authority of PCT/US2015/058669; Feb. 1, 2016; 11 pages.

Patent Cooperation Treaty; International Search Report and Written Opinion of the International Searching Authority of PCT/2014/055643; Dec. 29, 2014; 9 pages.

Patent Cooperation Treaty; International Preliminary Report on Patentability and Written Opinion of the International Searching Authority of PCT/2014/055643; Mar. 22, 2016; 6 pages.

Espacenet; Machine Translation of Bibliographic Data of JP2005530559A; as early as Feb. 22, 2016, 30 pages.

Google; Machine Translation of CN103989501B; Google Patents; as early as Feb. 21, 2020; 7 pages.

Patent Translate; Machine Translation of DE29720952U1; Patent Translate Powered by EPO and Google; as early as Aug. 18, 2021; 17 pages.

Google Translate; Machine translation of EP0159453A1; Google Patents; as early as Mar. 16, 2022; 7 pages.

Patent Cooperation Treaty, International Search Report and Written Opinion for PCT/IB21/53384; Aug. 18, 2021; 13 pages.

DE102006031092B3; "Google Machine Translation of DE102006031092B3"; as early as Mar. 20, 2020; 5 pages; Google translate.

(56) References Cited

OTHER PUBLICATIONS

J-Plat Pat; Machine Translation of JP3124027B; J-PlatPat; as early as Sep. 8, 2016; 6 pages.
Espacenet; Machine Translation of JP3124027B2; as early as Feb. 22, 2016; 6 pages.
European Patent Office, European Search Report including Supplementary European Search Report for EP15856303.1, Jun. 5, 2018, 8 pages.
Office Action (Non-Final Rejection) dated Nov. 20, 2023 for U.S. Appl. No. 17/365,344 (pp. 1-14).
Google; Machine Translation of CN103989501B; Google Patents; as early as Jun. 17, 2018; 11 pages.
J-Plat Pat; Machine Translation of JPS58138447A; J-Plat Pat; as early as Jul. 10, 2018; 5 pages.
Office Action (Final Rejection) dated Jul. 30, 2024 for U.S. Appl. No. 17/365,344 (pp. 1-15).

ANGLED EDGES
FOR STACKING
AROUND THE BEND

508

75°

114

275

271

276

128

277

273

278

130

3.00mm

512

114

130

271

128

132

MOVED NOTCH
UP HIGH

PUSHER MECHANISM

BEND (0.45mm)

506

114

295

60°

292

595

130

249

581

582

128

293

291

593

245

132

134

136

5.00mm 0.25mm 3.42mm

254

146

0.05mm
GAP

116

CHANGED
SHAPE OF
JAWS TO
ACCOMMODATE NEW
NOTCH POSITION

510

114

259

136

130

260

134

261

262

263

132

0.50mm 1.30mm

504

DETAIL A
SCALE 4:1

343

393

372

297

373

385

371

372

373

371

384

345

247

STACKED
CLIPS 10k

502

350

341

116

A

DETAIL G
SCALE 2:1

116

814

816

490

5deg 8.00mm BODY

VIEW WITH 5° TILT

G

METRx TUBULAR
RETRACTOR
Ø 26 x 80mm

810

116

812

EVERTED ENDS

247

DETAIL F
SCALE 2:1

104

DURA

806

349

348

350

481

Ø 25.03mm INNER
WORKING DIAMETER

482

483

480

402

497

496

808

80.00mm

F

393

297

DETAIL E
SCALE 4:1

296

2006

2014

SECTION D-D

E

296

2004

297

REDUCED "BOWING"
ON RAILS TO RETAIN
CLIPS BETTER

2012

D

D 5.61mm

INCREASED
THIS
DISTANCE
TO INCREASE
TRANSITION
RADIUS

TRANSITION RADIUS
LARGER SO CLIPS
CAN TRAVEL
WITHOUT DEFORMING
OR GETTING STUCK

391

2002

DETAIL C
SCALE 4:1

247

318

337

2010

383

SECTION B-B

C

2008

B

B

CLIPS AND APPLICATOR FOR TISSUE CLOSURE

CROSS REFERENCE TO RELATED APPLICATIONS

The present application is a Continuation of and claims priority to U.S. patent application Ser. No. 15/853,324, filed Dec. 22, 2017, entitled "Clips and Applicator for Tissue Closure," which is a Continuation of and claims priority to U.S. patent application Ser. No. 14/930,595, filed Nov. 2, 2015, entitled "Clips and Applicator for Tissue Closure" (now U.S. Pat. No. 9,883,866), which claims priority to U.S. Provisional Patent Application No. 62/074,212, filed Nov. 3, 2014, entitled "Bioabsorbable Clips and Applicator for Tissue Closure," the entire disclosures of which are hereby incorporated by reference in their entirety.

This invention was made with government support under TR000128 awarded by the National Institutes of Health. The government has certain rights in the invention.

TECHNICAL FIELD

Embodiments herein relate to surgical clips and surgical clip applicators used in tissue closure.

BACKGROUND

The brain and spine are covered with a tough outer membrane called the dura mater, or dura. During surgical procedures, e.g., spinal surgery, the dura mater may be opened intentionally or inadvertently. Such an opening is called a durotomy or dural tear. Dural tears requiring closure or repair have been reported to occur in a significant percentage of surgical procedures. In some approaches, sutures are used to repair or close the dura. Durotomies must be closed prior to closing the skin. Failure of the closure can result in persistent cerebrospinal fluid (CSF) leakage, for example. This leakage may result in wound breakdown, spinal headaches, infection, meningitis, and other consequences.

Minimally invasive surgeries (MIS) are becoming more commonly used during surgical procedures, e.g., to treat a variety of pathologies including herniated discs, spinal stenosis, synovial cysts, spondylolisthesis, deformity, intradural tumors, etc. Such procedures use smaller incisions to decrease intraoperative blood loss, reduce tissue disruption, decrease postoperative pain, and decrease lengths of hospital stays, for example.

Minimally invasive surgeries make use of smaller ports and result in less tissue disruption than traditional procedures. However, should a durotomy occur using a minimally invasive surgery, closure of the dura can become extremely difficult or impossible due to the small size of the incision. For example, in the setting of minimally invasive spine surgery, the ability to close a durotomy may be compromised when suture material cannot be manipulated sufficiently to achieve tight closure. Thus, due to the physical limitations of small working areas, repair of a durotomy may be technically difficult and time-consuming when using conventional suture and knot-tying techniques.

In order to overcome these technical difficulties resulting from minimally invasive surgeries, metal staples, such as titanium staples, delivered via a suitable applicator may be crimped or bent from an open position into a closed position around the tissue edges to close a hole in a tissue such as a durotomy. However, in such approaches, it is necessary to place the staples sufficiently close together along a dura tear in order to close the tissue since such staples may be too thin to cover and hold significant lengths along the tissue break. Further, use of metal staples or clips either results in a permanent foreign body left in the tissue or a second surgical intervention to remove the staples or clips. Clips or staples left in the tissue may interfere with postoperative imaging resulting in undesirable artifacts in radiographic imaging such as magnetic resonance imaging (MRI) and computed tomography (CT) scans.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

DETAILED DESCRIPTION OF DISCLOSED EMBODIMENTS

Figure 1:
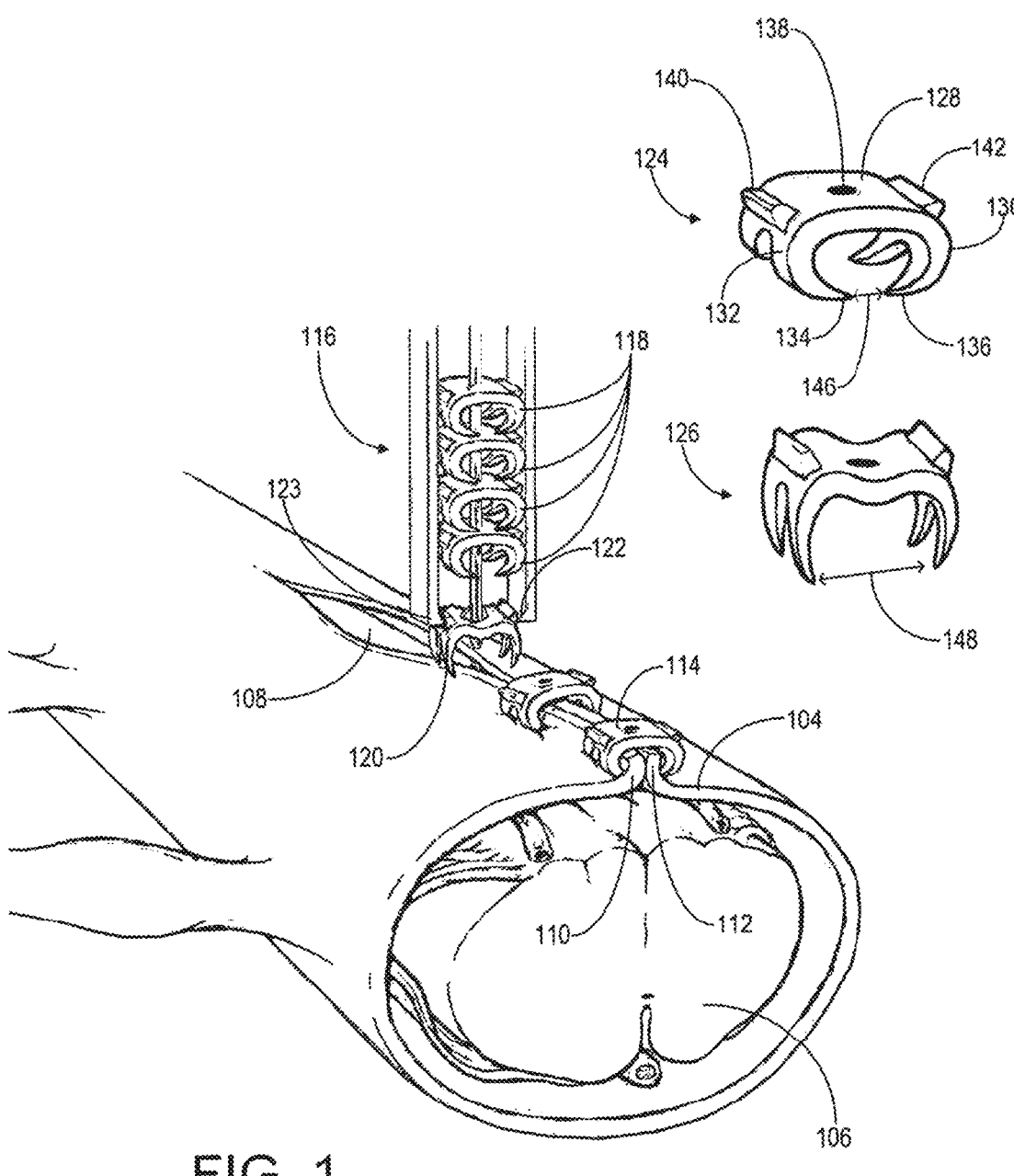
FIG. 1 shows an illustration of a surgical applicator applying example surgical clips to close a durotomy in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense.

Various operations may be described as multiple discrete operations in turn, in a manner that may be helpful in understanding embodiments; however, the order of description should not be construed to imply that these operations are order-dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements are in direct physical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A) B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

The present disclosure is directed to surgical clips and surgical applicators that may be used in performing rapid tissue closure in either minimally invasive surgeries or traditional open procedures. In particular, the surgical clips described herein are intended for use in closing durotomies, particularly durotomies resulting from minimally invasive surgeries.

A surgical applicator may be used to deliver the clips down a small opening, thereby obviating the need for sutures and knot tying to close the durotomy. An array of stacked surgical clips may be loaded into inwardly-turned tracks in a chamber or reservoir of the surgical applicator. A force may be applied to push a clip in the tracks towards a tip of the surgical applicator. The sides of that clip may be held within tracks at the tip of the applicator such that the mouth of the clip opens around the everted tissue edges of the dura, for example. Upon release of the clip from the applicator, the clip may grasp the everted edges, pulling the edges towards one another, closing the opening in the tissue. A force may again be applied to the next clip in the array so that the next clip is pushed into position to be opened at the mouth of the applicator for a subsequent application.

Disclosed herein is a surgical clip that includes opposing sides extending from a top portion. Each of the opposing sides may be convex. The opposing sides terminate at tips positioned below the top portion. The resting position of the clip is its closed position, and in the closed position, the tips are set at a first distance apart. Edges of the top portion and the first and second opposing sides form opposing front and back faces perpendicular to the first and second opposing sides. The front and back faces are angled inwardly towards each other at a region of the faces adjacent to the top portion. A first groove is formed in the first side. The first groove extends from the front face to the back face and has a top inner surface formed by a bottom surface of a region of the top portion extending over the first side. A second groove is formed in the second side. The second groove extends from the front face to the back face. The second groove has a top inner surface formed by a bottom surface of a region of the top portion extending over the second side. The first groove is substantially parallel to the second groove and the first and second grooves are substantially perpendicular to the front and back faces at a region of the front and back faces adjacent to the first and second tips. The first and second grooves are each configured to engage inwardly turned tracks at an end of a clip applicator such that, when a force is applied to the clip, the first and second sides bend outwardly away from each other, thereby increasing the distance between the tips to a second distance between the tips to place the clip in an open position. In the open position, the distance between the tips is greater than the distance between the tips in the closed position. In some embodiments, the width of the clip may be at least 25% of the length of the clip (length is the dimension from the end of the first side to the end of the second side, while width is the dimension of the clip perpendicular to the length). In some embodiments, each tip may be made up of at least two tabs. Each tab may converge in a direction towards the opposing tip to form two opposing pairs of teeth. In some embodiments, the first and second grooves may be each configured to engage inwardly turned tracks at an end of a clip applicator such that when a push rod of the clip applicator is used to apply pressure to the top portion, the first and second sides bend outwardly away from each other, thereby increasing the distance between the tips to the second distance between the tips. In alternative embodiments, the first and second grooves may be each configured to engage inwardly turned tracks of a clip applicator, where a distance between the inwardly turned tracks decreases at an end of the clip applicator, such that when a force is applied to the back face of the clip, the clip moves within the tracks toward the end of the clip applicator thereby increasing the distance between the tips to the second distance between the tips.

Disclosed herein is an array of surgical clips. The array comprises two or more of the clips described above and a chamber housing the array of clips. The chamber has inwardly turned tracks engaging the grooves of each clip to maintain the front and back faces of each clip as orientated in the same direction as the front and back faces of the other clips in the plurality of surgical clips, yet large enough to allow movement of the plurality of clips in the direction of the faces of the clips. The clips in the array can also be in physical contact with one another. In some examples, a direction of the inwardly turned tracks may transition from a vertical direction to a horizontal direction in a transition region of the tracks and the angled regions of the faces of adjacent clips in the transition region may interface with each other.

Disclosed herein is a surgical clip applicator. The applicator includes a clip array within a chamber as described above and a pushing element configured to apply pressure to a top clip in the array. The applicator can also have a grating in a front wall or a back wall of the chamber. The grating may extend from the transition region of the tracks in a direction away from an open end of the chamber to hold the tracks in place and permit a user to view the clips in the applicator.

Since everted tissue edges are grasped by the surgical clip in such an approach, a risk of adhesion to the underlying spinal cord may be potentially reduced. Further, by applying a force to open such a surgical clip from a closed, resting state to an intermediate open state and then releasing the force to permit the clip to close to its resting state around the dural tissues, a greater amount of control may be conferred to the final closed state of the clip around the tissues to provide pressure on the dura leaflets for maintaining closure of the durotomy.

In this way, closure of the dura using a small bioabsorbable clip to grasp but not penetrate the tissue edges and maintain tension until the tissues heal may be applied quickly, easily, and in rapid succession by using an applicator. Such an approach may potentially increase speed and ease of clip application, decrease the risk of CSF leakage, decrease intradural adhesions due to non-penetration of the clip, reduce risk of adhesion to the underlying spinal cord, minimize dural exposure, and decrease expensive operative time. Further, such an approach may also be used in other surgical arenas where reapproximation is desired; including, for example, cranial surgery for closure of the dura, general surgery for closure of hollow organs, urologic surgery for closure of the bladder, closure of uereters and other tubular structures, and gynecological procedures for closure of reproductive structures.

The following description relates to bioabsorbable surgical clips and surgical applicators for performing rapid water-tight tissue closure in minimally invasive or traditional open procedures. For example, as illustrated in FIG. 1, a surgical applicator 116 may be used to deliver one or more surgical clips, e.g., clips 118, to assist in tissue closure. In FIG. 1, a dural tear or durotomy 108 is shown in the dura mater 104 around a spinal cord 106. As remarked above, the dura mater is a tough outer membrane covering the brain and spinal cord which may be opened intentionally or inadvertently during surgical procedures.

The surgical clips may be composed of any material including any suitable bioabsorbable or resorbable material. The terms bioabsorbable and resorbable are used herein to mean dissolving inside the human body after a period of time. In some examples, the bioabsorbable material may be chosen based on a time duration at which the material dissolves. For example, the bioabsorbable material may have the property that it does not substantially dissolve within seven days after installation along the tissue but dissolves any time after one week while maintaining structural integrity before then. For example, the bioabsorbable material may comprise a biocompatible, bioabsorbable polymer such as Poly-L-Lactic Acid/Poly glycolic acid (PLLA/PGA), Polycapralactone, Polydioxanone or some combination thereof. By using a bioabsorbable material, no permanent foreign body is left in the tissue following surgery. Further in some examples, the clip may be composed of a material that is radiolucent, e.g., invisible or transparent to x-rays, as well as bioabsorbable. For example, the surgical clips may be composed of a suitable material which is radiolucent and bioabsorbable so that substantially no undesirable artifacts from the clips appear in radiographic imaging e.g., in magnetic resonance imaging (MRI) and computed tomography scans (CT). Further, by using a bioabsorbable and radiolucent material, surgical clips with a wide footprint may be used to cover a greater length along the tissue thereby potentially decreasing a number of clips needed to reliably seal the tissue in a water tight fashion. Additionally, in some examples, the clips may be composed of materials, e.g., polymers, selected to achieve a predetermined amount of strength, flexibility, and/or other mechanical properties of the clip.

As illustrated in FIG. 1 at 124, a surgical clip used to close a durotomy may comprise a first side 132 and a second side 130, where the second side 130 opposes the first side 132. The first and second opposing sides 132 and 130 extend from a top portion 128 of the clip and terminate at first and second tips positioned below the top portion 128. For example, the first side 132 is coupled to and extends from top portion 128 and terminates at a first tip 134 positioned below the top portion 128. Likewise, the second side 130 is coupled to and extends from top portion 128 and terminates at a second tip 136 positioned below the top portion 128. In an installed, closed position, the tips 134 and 136 of the surgical clip may grasp but not penetrate or pierce everted tissue edges. For example, in FIG. 1 surgical clip 114 is shown in an installed position along the durotomy 108 grasping everted tissue edges 112 and 110. The surgical clips may include a variety of features and may have a variety of shapes and dimensions, examples of which are described below with reference to the scaled drawings of FIGS. 2-23. In some embodiments, the clip may have a length in a range from 3-5 millimeters (mm), a height in a range of 3-5 mm, a width in a range of 3-5 mm, and a diameter (if cylindrically shaped) in a range of 3-5 mm. In some examples, the top portion 128 of the clip may include an aperture 138, slots, and/or other features used to achieve a particular bending moment of the surgical clip. For example, as described in more detail below, sides of the surgical clip may be temporarily bent outward by applying a force to the clip while holding the sides in place to install the clip over everted tissue edges. In some examples, a size of a slot or aperture or a thickness of the top portion of the clip may be selected so that the clip confers an optimal amount of force to grasp the tissue while maintaining the ability to be temporarily opened via engagement with tracks of the surgical applicator during an installation of the clip. For example, the clip may be designed to withstand at least 10 cmH2O pressure (e.g., prostrate pressure) without leakage and may, in some examples, be designed to withstand 20 cmH2O (e.g., standing lumbar pressure) without leakage. Further, the material selected may be based on a desired elasticity for applying a predetermined holding force to the tissue for a predetermined duration following installation of the clip around everted tissue edges.

The clip may include features that are configured to engage with the surgical applicator to assist in installation of the clip around edges of a tissue break. For example, the surgical clip may include grooves, cut-outs, notches, tabs or other suitable features that engage tracks or protrusions of the surgical applicator, e.g., which engage protrusions 122 and 123 of surgical applicator 116 shown in FIG. 1. The example clips shown in FIG. 1 include tabs extending outwardly from the first and second sides of the clip. For example, a tab 140 is shown extending outwardly from first side 132 and may be configured to engage with protrusion 123 of the applicator 116 and tab 142 is shown extending outwardly from second side 130 and may be configured to engage protrusion 122 of the applicator. However, in other examples, such tabs may be omitted or other alternative engagement features may be included on the opposing sides of the clip, examples of which are shown in FIGS. 2-23 described below.

As illustrated in FIG. 1, a stack of surgical clips 118 may be loaded into the surgical applicator 116 for quick successive delivery of surgical clips to grasp everted tissue edges, e.g., the bent and interfacing tissue edges 112 and 110, to close the durotomy. For example, as shown in FIG. 1, an installed surgical clip 114 grasps but does not penetrate or pierce the everted edges of the dura thereby holding the edges together. Surgical applicator 116 may be used to deliver the clips down a small opening during minimally invasive procedures thereby potentially obviating the need for sutures and knot tying to close the dura. In one example approach, an array of stacked surgical clips 118 may be loaded into a chamber or reservoir of the surgical applicator and a downward force from a push rod or other pushing element in the chamber may be used to push the center of a clip located at a tip of the surgical applicator, e.g., clip 120 shown in FIG. 1, while the sides of that clip are firmly held at the tip causing the mouth of the clip to open around the everted tissue edges 110 and 112 of the dura. To release the clip, the push rod or pushing element may be retracted allowing the clip to grasp and reapproximate the two dural edges 110 and 112. The push rod or pushing element can then retract further to engage the next clip in the reservoir so that the next clip is pushed into position to be opened at the mouth of the applicator for a subsequent application to the everted tissue edges. It should be understood that the use of a push rod to eject the clip is provided by way of illustration and any other suitable pusher or ejector feature may be included in the clip applicator. Further, the term "push rod" as used herein may refer to any such suitable pusher or ejector feature of the applicator used to deploy the clips. In alternative embodiments, examples of which are described below with regard to FIGS. 2-23, an array of clips may be loaded into inwardly turned tracks within a clip applicator and a force may be applied to a top clip in the array of clips to push the clips around a bend in the tracks. A distance between the tracks may decrease at an end of the applicator such that when a clip is pushed toward the end of the applicator within the tracks, the clip is forced into a temporary open position until it disengages with the tracks and returns to its closed, resting position.

The surgical clips have a closed resting configuration which can be substantially the same before and after installation along the tissue edges. During installation with the surgical applicator, the surgical clips have an intermediate open state formed by engagement of the clip with features of the surgical applicator during the installation of the clip. By applying a force to the clip while sides of the clip are engaged with features of the surgical applicator, a reversible deformation of the clip from a closed resting position to an intermediate open position may occur. This deformation is recoverable once the clip disengages with the engagement features of the applicator after the clip is positioned around the tissue edges so that the clip returns to its closed resting position to grasp the everted edges.

FIG. 1 shows an example clip in a closed resting state at 124 and in the intermediate open state at 126. In the closed resting state there is a first distance 146 between the first and second tips 134 and 136. In this closed position, the first distance may be selected so as to provide a sufficient amount of space between the tips 134 and 136 to accommodate a thickness of the everted tissue edges to which it is to be applied (e.g., enough space to accommodate twice the thickness of the dura) while maintaining sufficient gripping force on the everted tissue edges after application. The first side 132 and the second side 130 of the clip are configured to engage the clip applicator such that, when the clip applicator is used to apply a pressure to the clip, the first and second sides bend outwardly away from each other thereby increasing the distance between the tips to a second distance 148 greater than the first distance 146 so that the clip is temporarily deformed to an open position for installation around the tissue edges. In some examples, this second distance 148 may be a predetermined distance, e.g., at least 3 mm, achieved via forces applied to the clip from the clip applicator.

By applying a force to open such a surgical clip from a closed, resting state to an intermediate open state and then releasing the force to permit the clip to again close to its resting state around the dural tissues, a greater amount of control may be conferred to the final closed state of the clip around the tissues to provide an optimal pressure on the dura leaflets for maintaining closure. For example, the grasping force of the closed resting state of such a clip may be tailored to a specific type or thickness of tissue to which it is to be applied.

FIGS. 2-23 described below show scaled drawings of various example embodiments of surgical clips and surgical clip applicators. The example numerical dimensions shown in these figures are in millimeters (mm). Further, like-numbered elements used throughout the figures correspond to like elements.

Figure 2:
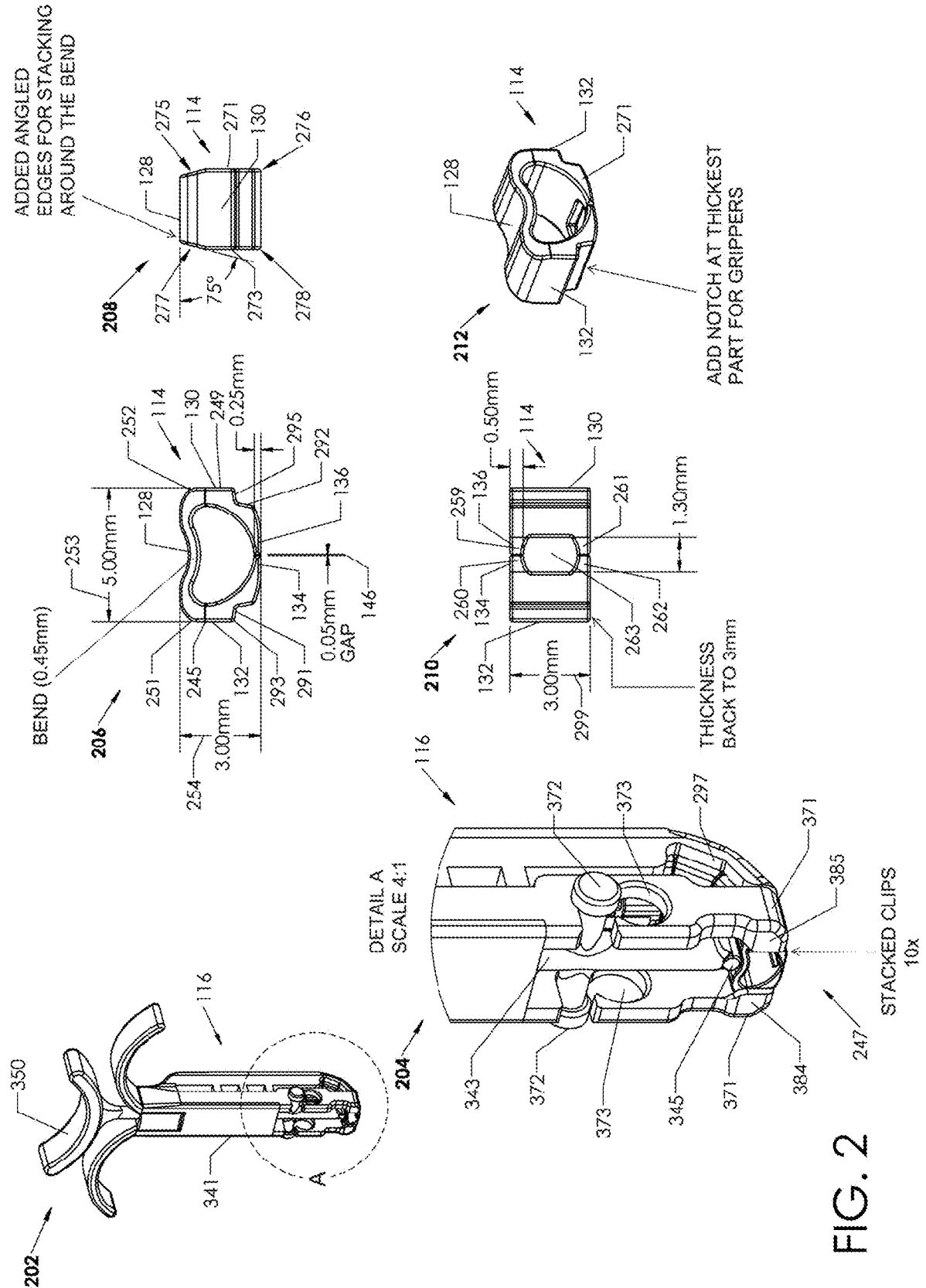
FIGS. 2-23 show scaled drawings of example surgical clips and example surgical clip applicators in accordance with various embodiments.
Figure 3:
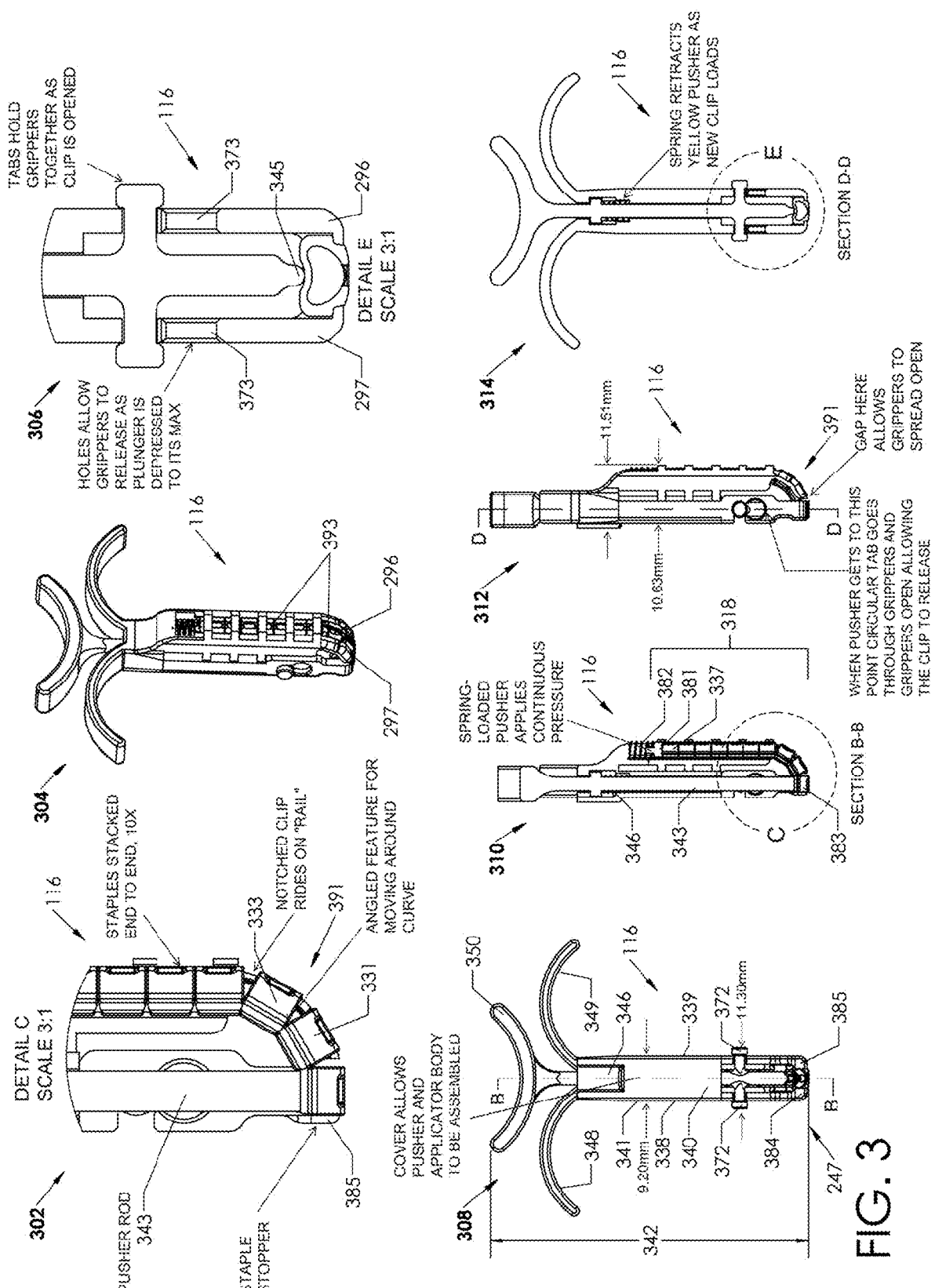
Figure 4:
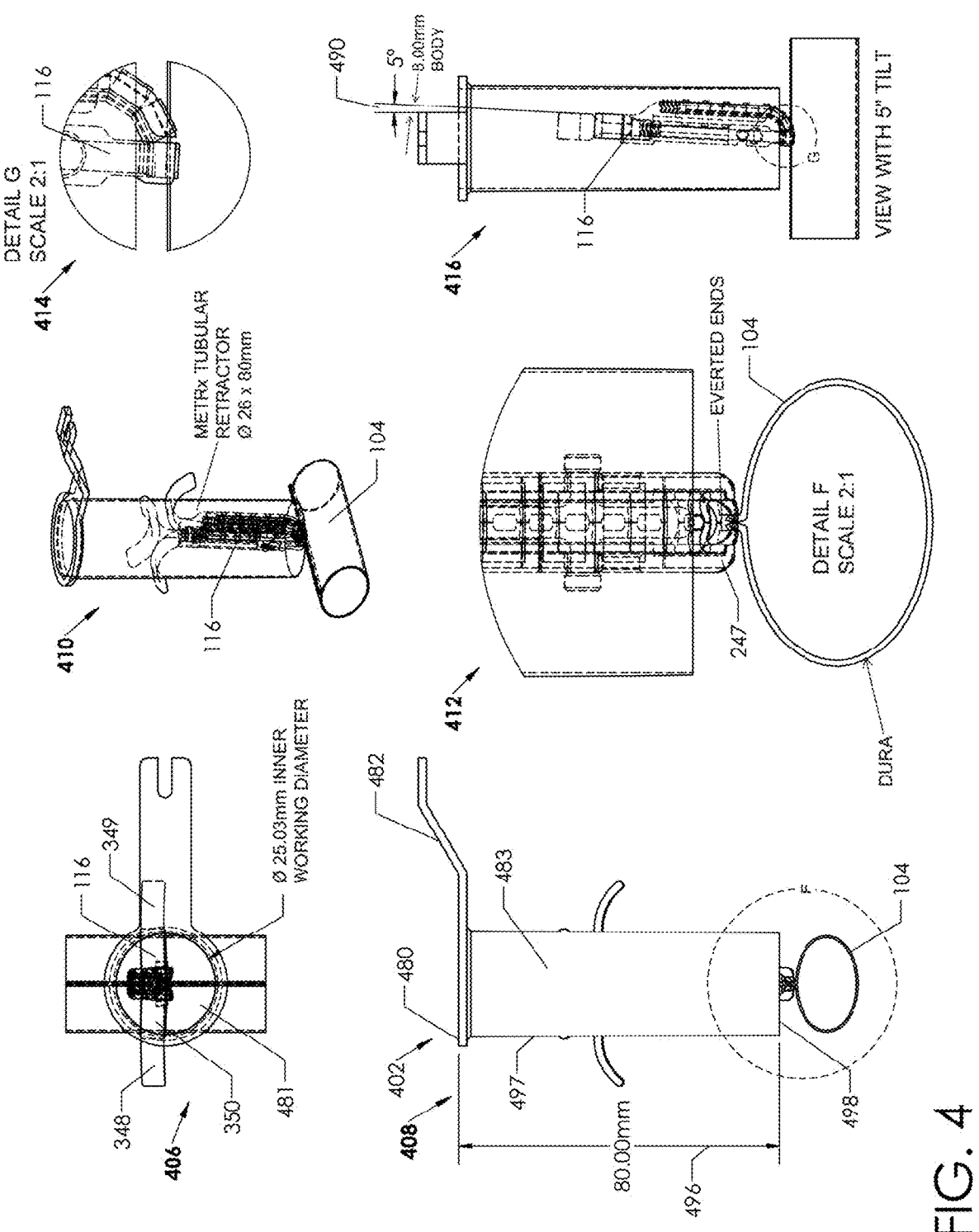

Turning to FIGS. 2-4, a first example embodiment of a surgical applicator 116 and surgical clip 114 is shown from various perspectives and cross-sections. At 206, 208, 210, and 212, various viewpoints of the first example embodiment of a surgical clip 114 are shown. In particular, a front face view of example clip 114 is shown at 206, a side view of clip 114 is shown at 208, a bottom view of clip 114 is shown at 210, and a perspective view of clip 114 is shown at 212.

Clip 114 comprises a concave top portion 128 with opposing sides 130 and 132 extending therefrom. In particular, a first side 132 is coupled to top portion 128 via a rounded junction 251 and curves inwardly from junction 251 to a tip 134 positioned below top portion 128. Likewise, a second side 130 is coupled to top portion 128 via a rounded junction 252 and curves inwardly from junction 252 to a tip 136 positioned below top portion 128. A thickness of each tip of the opposing tips 136 and 134 tapers or decreases in a direction toward the opposing tip so that each tip of the opposing tips 136 and 134 converges in a direction towards the opposing tip. The concave top portion 128 curves toward the interior of the clip in the center of the top portion so that a minimum height of the clip occurs at the center of the top portion. The opposing sides 130 and 132 and the rounded junctions 251 and 252 coupling the sides 132 and 130 to the top portion form a heart-shaped face as seen in view 206.

In this example, each of the first and second opposing sides 132 and 130 of the clip comprises a flat portion coupled via a curved top junction to the top portion 128. For example, flat portion 249 is included in side 130 and flat portion 245 is included in side 132. Flat portion 249 may be parallel with flat portion 245 when the clip is in the closed position.

Edges of the top portion 128 and the first and second opposing sides, 132 and 130, form opposing front and back faces 271 and 273, respectively, perpendicular to the first and second opposing sides. As shown at 208, the front face 271 and back face 273 are angled inwardly towards each other at a region of the faces adjacent to the top portion 128. In this example, the region 275 of the front face adjacent to the top portion 128 is inwardly angled by approximately 15 degrees relative to the region 276 of the front face adjacent to the first and second tips. Likewise, the region 277 of the back face adjacent to the top portion is inwardly angled by approximately 15 degrees relative to the region 278 of the back face adjacent to the first and second tips.

Each of the first and second tips 134 and 136 converges in a direction towards the opposing tip to form two opposing pairs of teeth. For example, tip 134 comprises a first tooth 260 and a second tooth 262 and tip 136 comprises a first tooth 259 and a second tooth 261. Each tooth of a tip converges in thickness and width to an edge facing an opposing tooth on the other tip. For example, a width and thickness of tooth 260 on tip 134 decreases in a direction toward the opposing tooth 259 on tip 136 and a width and thickness of tooth 262 on tip 134 decreases in a direction toward the opposing tooth 261 on tip 136. Teeth 259 and 261 on tip 136 likewise converge to the opposing teeth on tip 134 so that an aperture 263 is formed in the bottom of the clip between teeth of the tips. In some examples, this aperture 263 may have a circular shape with a predetermined diameter, e.g., a diameter of 2.5 mm. In alternative examples, as shown at 210, aperture 263 may have a rounded rectangular shape. It should be understood that the aperture formed between the teeth of the tips on the bottom of the clip may have any suitable diameter or shape, e.g., oval-shaped, rectangular, diamond-shaped, etc. The teeth may be used to hold everted edges of tissue in place while not-penetrating and not piercing the tissue when repairing a durotomy, for example. One of skill in the art in light of this disclosure would understand how to make tips 134 and 136 of sufficient sharpness to grasp but not penetrate or pierce everted edges of a tissue such as a dura without undue experimentation.

Each of the first and second sides 132 and 130 includes a groove or notch configured to engage tracks in surgical applicator 116. In particular, a first groove 291 is formed in the first side 132. The first groove 291 extends from the front face 271 to the back face 273. The first groove has a top inner surface 293 formed by a bottom surface of a region of the top portion 128 extending over the first side 132. Likewise, a second groove 292 is formed in the second side 130. The second groove 292 extends from the front face 271 to the back face 273. The second groove 292 has a top inner surface 295 formed by a bottom surface of a region of the top portion extending over the second side 130. The first groove 291 is substantially parallel to the second groove 292 and the first and second grooves are substantially perpendicular to the front and back faces at a region of the front and back faces adjacent to the first and second tips, e.g., regions 276 and 278.

The first and second grooves, 291 and 292, are each configured to engage inwardly turned tracks 296 and 297 of a clip applicator 116 such that, when a force is applied to the clip, the first and second sides bend outwardly away from each other, thereby increasing the distance between the tips to a second distance between the tips, wherein the second distance between the tips is greater than the first distance between the tips, thereby placing the clip in an open position.

The example clip 114 has a height 254 extending in a direction from a midpoint of the opposing tips 134 and 136 towards the top portion 128, a length 253 extending in a direction from first side 132 towards second side 130, and a width 299 extending from the front face 271 of the clip towards the back face 273 of the clip in a direction perpendicular to length 253. In this example, the height 254 is less than the length 253 and the height is substantially the same as the width 299. For example, the length may be approximately 5 mm and the height and width may both be approximately 3 mm; however, it should be understood that these dimensions are provided by way of example and are not intended to be limiting. Any suitable height, length, and width may be used.

The surgical clip 114 is shown in views 206, 208, 210, and 212 in a closed resting position with a first distance 146 between opposing tips 134 and 136. For example, this first distance 146 between the tips may be approximately 0.05 mm when the clip is in its resting closed state. A length of this first distance 146 may be based on a type and thickness of tissue to which it is to be applied. For example, the first distance 146 may be greater for applications on a thicker tissue.

Though not shown in FIG. 2, in some examples, the top portion 128 may be substantially flat when the clip is in the resting state (e.g., as shown in FIG. 1), but may become concave or temporarily bent inward during a transitional intermediate open state of the clip during installation of the clip using clip applicator 116. In particular, tracks 296 and 297 of clip applicator 116 may engage grooves 291 and 292 of clip 114 so that clip 114 is moveable within the tracks. A force may be applied to the clip to move the clip in the tracks towards the distal end 247 of the surgical applicator. In some examples, while the grooves are engaged with the tracks at the distal end 247, a force may be applied to the top portion of the clip so that the distance between the tips of the clip increases to a second distance greater than the first distance

146, e.g., greater than 0.05 mm, so that the tips of the clip are opened for installation of the clip around everted tissue edges. This second distance may be a distance of at least a predetermined amount, e.g., at least 3 mm. Alternatively, as described below, a force may be applied to the back face 273 of the clip to move the clip within the tracks towards the distal end 247 of the surgical applicator. In this example, a distance between the tracks may decrease at the distal end 247 of the applicator 116 so that when the clip is forced toward the distal end, the clip is at least partially placed into the open position.

Various views and cross-sections of an example surgical applicator are shown at 202, 204, 302, 304, 306, 308, 310, 312, and 314 in FIGS. 2-3. In particular, at 202, a perspective view of example surgical clip applicator 116 is shown. At 204, a detailed view is shown of a distal end 247 of the applicator 116 in the region A shown in view 202. The view 204 is shown at a scale of 4:1 relative to the view shown at 202. At 308 a front view of applicator 116 is shown. At 310, a cross-section of applicator 116 is shown along section B-B shown in view 308. View 302 shows a detailed view of section C shown in view 310, where view 302 is shown at a scale of 3:1 relative to view 310. View 312 shows a side view of applicator 116. View 314 shows a cross-sectional view along cross-section D-D in view 312. View 306 shows a detailed view of region E shown in view 314 and is shown at a scale of 3:1 relative to view 314. View 304 shows a perspective view of applicator 116.

With reference to views 202, 204, 302, 304, 306, 308, 310, 312, and 314 shown in FIGS. 2-3, the surgical applicator 116 comprises an elongated body 341 defining a chamber with an open end 247 within which a push rod 343 is contained. The push rod 343 extends away from the open end 247 of the surgical clip applicator and terminates at a thumb pusher element 350. The thumb pusher element 350 comprises a curved handle shaped to fit a thumb of a user. The clip applicator further includes two opposing finger grasping elements 348 and 349 coupled to the elongated body 341. For example, a user may grip the finger grasping elements 348 and 349 with two fingers and apply a downward force to the thumb pusher element 350 to urge the push rod downward toward the distal end 247 in order to apply a force to one or more clips in the chamber of the applicator.

Different sizes of the applicator may be available depending on a quantity of clips desired (e.g., an applicator may house 5-30 clips). For example, the applicator may come in different lengths depending on the type of surgery to be performed and the tissue on which the surgery will be performed. A short handle applicator may be used for open surgeries while a longer handle applicator may be used for deeper, smaller portals generated by minimally invasive surgical procedures. For example a height 342 of the applicator 116 may be in a range of 125-150 mm (~5-6 inches) for minimally invasive procedures. The applicator may be used by right or left-handed neurosurgeons and may utilize activation mechanisms that are standard or familiar to neurosurgeons. For example, the activation mechanism of the applicator may utilize a pistol grip design, a syringe plunger-type design, a looped-end forcep design, etc. Further, the applicator may be activated by fingers of a user rather than whole-hand activation for increased dexterity and fine motor control.

An array or stack of surgical clips 318 is included within a chamber or reservoir within the walls of the elongated body 341 of the applicator. The chamber has inwardly turned rails or tracks 296 and 297 engaging the grooves of each clip to maintain the front and back faces of each clip as orientated in the same direction as the front and back faces of other clips in the plurality of surgical clips, yet large enough to allow movement of the plurality of clips in the direction of the faces of the clips. For example, the stack of surgical clips 318 may comprise two or more clips in physical contact with one another. A direction of the inwardly turned tracks transitions from a vertical direction to a horizontal direction in a bend or transition region 391 of the tracks. In the transition region 391, the angled regions of the faces, e.g., angled regions 275 and 277 shown at 208, of adjacent clips in the transition region interface with each other. For example, as shown at 302, the angled portion of the back face of clip 331 physically touches the angled portion of the front face of adjacent clip 333 in the transition region 391. The angled portions of the clips permit the clips to be stacked while they transition from a vertical to a horizontal direction around a bend or transition region of a surgical applicator. This allows the clips to be stacked but then dispensed individually and may accommodate flexure of the clips as a force is applied to dispense the clips.

In some examples, the array of stacked clips may be loaded into the chamber of the surgical applicator as a group rather than individually. For example, a user may obtain a package of a predetermined number of pre-stacked and pre-aligned surgical clips, e.g., including five or more individual clips stacked face to face with each other and oriented in the same direction, and may load this package of clips into the tracks of the surgical applicator, e.g., via an entry point comprising an opening at a top end of the applicator. As another example, an array of surgical clips may be preloaded into the applicator so that an end user receives a fully assembled pre-packaged applicator including a pre-loaded quantity of clips loaded within the chamber. Such a pre-packaged surgical clip applicator may have any suitable number of clips contained therein, e.g., 5, 10, 15, or 30 clips per applicator. The number of clips included in an applicator may depend on a particular surgical application. For example, the number of clips included in a clip array may depend on a particular surgical application or a length of the tissue tear to which the clips are to be applied. Such a pre-packaged, pre-loaded surgical clip applicator may be sterilized and suitably wrapped and, in some examples, may be disposable after use and may include labeling which indicates various parameters associated with the surgical applicator and clips therein such as dimensional information, disclaimer information, clip material composition, etc.

The array of stacked clips includes a top clip 337 which is in contact with a spring-loaded pusher element 381 in contact with the back face of top clip 337. A spring 382 interfaces with pusher element 381 in the clip applicator to apply a continuous downward pressure to the stack of clips in the applicator. In particular, the spring-loaded pusher element 381 biases the stack of clips 318 toward the distal end 247 of the applicator 116.

The array of stacked clips also includes a bottom clip 383 at the distal end 247 of applicator 116. The front face of the bottom clip 383 interfaces with stopper elements 384 and 385, which prevent the bottom clip from moving in a direction perpendicular to the front and back faces of the bottom clip towards the front face of the bottom clip. An end of the push rod 343 opposing the thumb pushing element 350 is in contact with the top portion of bottom clip 383. The bottom clip 383 may be held in position via engagement of the grooves or notches in the sides of the clip with the opposing tracks or rails 297 and 296 at the distal end 247 of the applicator.

In this example embodiment, the push rod 343 interfaces with a top portion of bottom clip 383 via a clip interfacing element 345 coupled to an end of the push rod 343 opposing the thumb pusher element 350. The clip interfacing element 345 may comprise a cylindrically-shaped element having a radius that complements the curvature of the concave top portion of the clip. Further, in this example, a spring 346 is included around a portion of the push rod between the thumb pusher element 350 and an inner wall feature within the chamber of the applicator. The spring 346 can comprise a wire spring encircling a portion of the push rod 343 which provides a biasing force to the push rod 343 in a direction away from the distal end 247 in order to return the push rod to an initial retracted position following an application of a downward force to the push rod via the thumb pushing element. However, in other examples, such a spring element may be omitted.

The surgical applicator 116 may also include grippers 371 at the distal end 247. Grippers 371 may comprise two opposing arms which are biased away from each other but are held in a closed position around the sides of bottom clip 383 when opposing circular tabs 372 extending from push rod 343 interface with outer surfaces of the grippers. In particular the tabs 372 hold the grippers 371 together for an initial duration while a downward force is applied via push rod 343 to the top portion of bottom clip 383 to open the clip. After the initial duration wherein the clip 383 is opened, application of the downward force via the push rod to the top portion of bottom clip 383 may be continued so that the tabs 272 are pushed into opposing aperture or holes 373 formed in opposing sides of body 341. The apertures 373 have diameters larger than the diameters of the circular tabs 372 so that when the tabs are moved into the apertures, constraint of the grippers by the tabs is released so that the opposing arms of the grippers move away from each other thereby releasing the clip from the distal end of the surgical applicator so that the open clip can be installed around everted tissues edges.

In some examples, a cover 340 may be included along a portion of at least one wall of the chamber of the surgical applicator. The cover 340 may comprise at least a portion of a wall of the applicator chamber perpendicular to side walls 338 and 339 of the chamber. In some examples, cover 340 may be composed of a transparent material. The cover may extend a distance along a wall of the chamber from above the tabs 372 toward the thumb pusher element to terminate at a location adjacent to spring 346. Cover 340 may be removable and may be used to assist in assembly of the applicator.

In some examples, applicator 116 may also include a grating 393 in a wall of the chamber housing the clips. The grating may extend along the tracks 297 and 296 and may comprise a plurality of parallel trusses, ribs, or support members where each truss, rib, or support member spans from one track to the opposing track to provide support to the opposing tracks 296 and 297.

FIG. 4 shows various viewpoints and cross-sections of an example surgical clip applicator system 402 which comprises a tubular retractor 497 within which clip applicator 116 may be inserted while performing a surgical procedure on dura 104. At 406, a top view of the surgical clip applicator system is shown. At 408, a side view of the surgical clip applicator system is shown. At 412, a detailed view of an end of the tubular retractor 497 is shown for the region F shown in view 408. At 410, a perspective view of the surgical clip applicator system with the applicator inserted into the tubular retractor 497 at an angle is shown. At 416, a side view of the surgical clip applicator system with the applicator inserted into the tubular retractor 497 at an angle 490 is shown. View 414 shows a detailed view of the region G shown in view 416.

Tubular retractor 497 may comprise a cylindrical body 483 defining an inner working aperture 481 extending from a top lip 480 to an open end 498 at the surgical site. The top lip extends around a circumference of the working aperture at a top open end of the tubular retractor 497 opposing the open end 498 and a circumference of the top lip may be greater than a circumference of the cylindrical body. For example, the inner working aperture may have a diameter of approximately 25 mm and may have a height 496 of approximately 80 mm so that applicator 116 can easily fit within the tubular retractor during a surgical procedure.

The tubular retractor 497 may further include a supporting element 482 coupled to the lip 480 at an end of the tubular retractor 497 opposing end 498. For example, during a surgical procedure, the tubular retractor 497 may be positioned via supporting element 482 so that end 498 encompasses a surgical working area over the tissues to be repaired. In order to close the tissue using the clip applicator, the applicator 116 may be inserted into the tubular retractor 497 so that the distal end 247 of the applicator extends beyond end 498 of the tubular retractor 497 toward the tissue tear so that a surgical clip may be applied to everted tissue edges along the tear.

As shown in view 416 the applicator may be tilted away from a central axis of the tubular retractor 497 so that an angle 490 is formed between a central axis of the applicator and a central axis of the tubular retractor 497, e.g., a 5° angle. In this way a clip may be applied using the applicator without obstructing the view of the surgeon applying the clips to the tissues.

Turning to FIGS. 5-8, another example embodiment of a surgical applicator 116 and surgical clip 114 are shown from various perspectives and cross-sections. At 506, 508, 510, and 512 various viewpoints of the second example embodiment of a surgical clip 114 are shown. In particular, a front face view of an example clip 114 is shown at 506, a side view of clip 114 is shown at 508, a bottom view of clip 114 is shown at 510, and a perspective view of clip 114 is shown at 512. The top portion 128 of the surgical clip shown in FIGS. 5-6 comprises two opposing wings, 581 and 582, which extend over the opposing sides 132 and 130. The grooves 291 and 292 are formed between top inner surfaces of the wings of the top portion and shelves 593 and 595 formed in each side. In particular, groove 291 has top inner surface 293 formed by a bottom surface of a region or wing 581 of the top portion 128 extending over the first side 132 and a bottom inner surface 593 formed as a top surface or shelf within side 132. Likewise, groove 292 has top inner surface 295 formed by a bottom surface of a region or wing 582 of the top portion 128 extending over the second side 130 and a bottom inner surface 595 formed as a top surface or shelf within side 130. In this example, the angle between the top inner surface 293 and the bottom inner surface 593 and the angle between the top inner surface 295 and the bottom inner surface 595 are both 60 degrees. However, in other examples, the angle between the top inner surfaces and the bottom inner surfaces of the grooves may be greater than 60 degrees or less than 60 degrees, e.g., 25 degrees. Further, when the clip is in the closed position, the bottom inner surface 593 may lie in the same plane as bottom inner surface 595.

Figure 6:
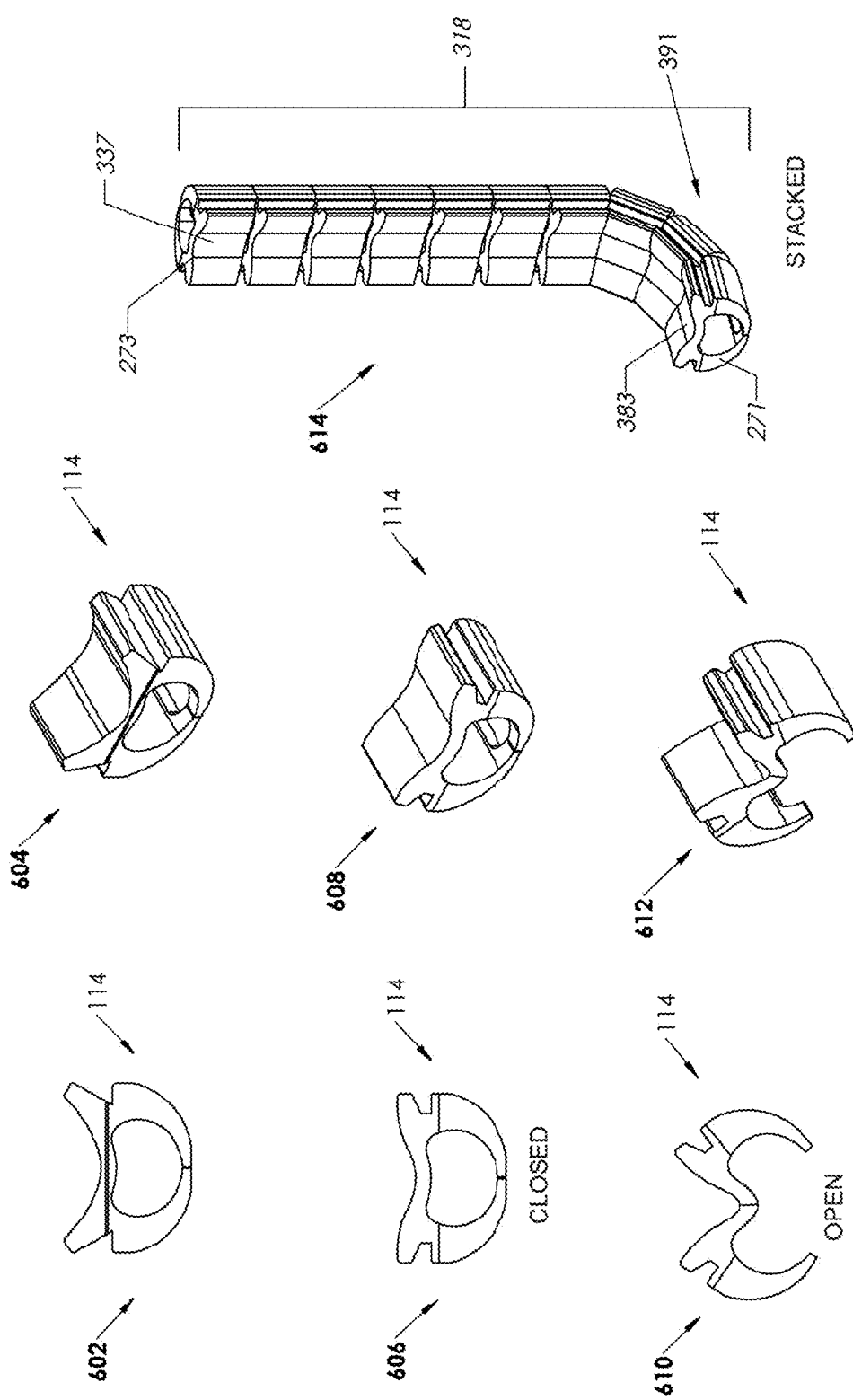

FIG. 6 shows additional embodiments of example surgical clips in the closed resting position in views 602, 604,

606, and 608 and in an intermediate open position in views 610 and 612. Additionally, in view 614 a stack of surgical clips 318 is shown. The stack of surgical clips comprises a top clip 337 having a back face 273 which is not in physical contact with another clip and a bottom clip 383 having a front face which is not in contact with another clip. In the stack 318, the faces of adjacent clips may be in physical contact with each other and the stacking of the clips may accommodate a transition region 391 where the orientation of the clips transitions from a vertical direction to a horizontal direction. In the transition region 391, the angled regions of the faces, e.g., angled regions 275 and 277 shown at 508, of adjacent clips in the transition region interface with or physically touch each other.

Figure 5:
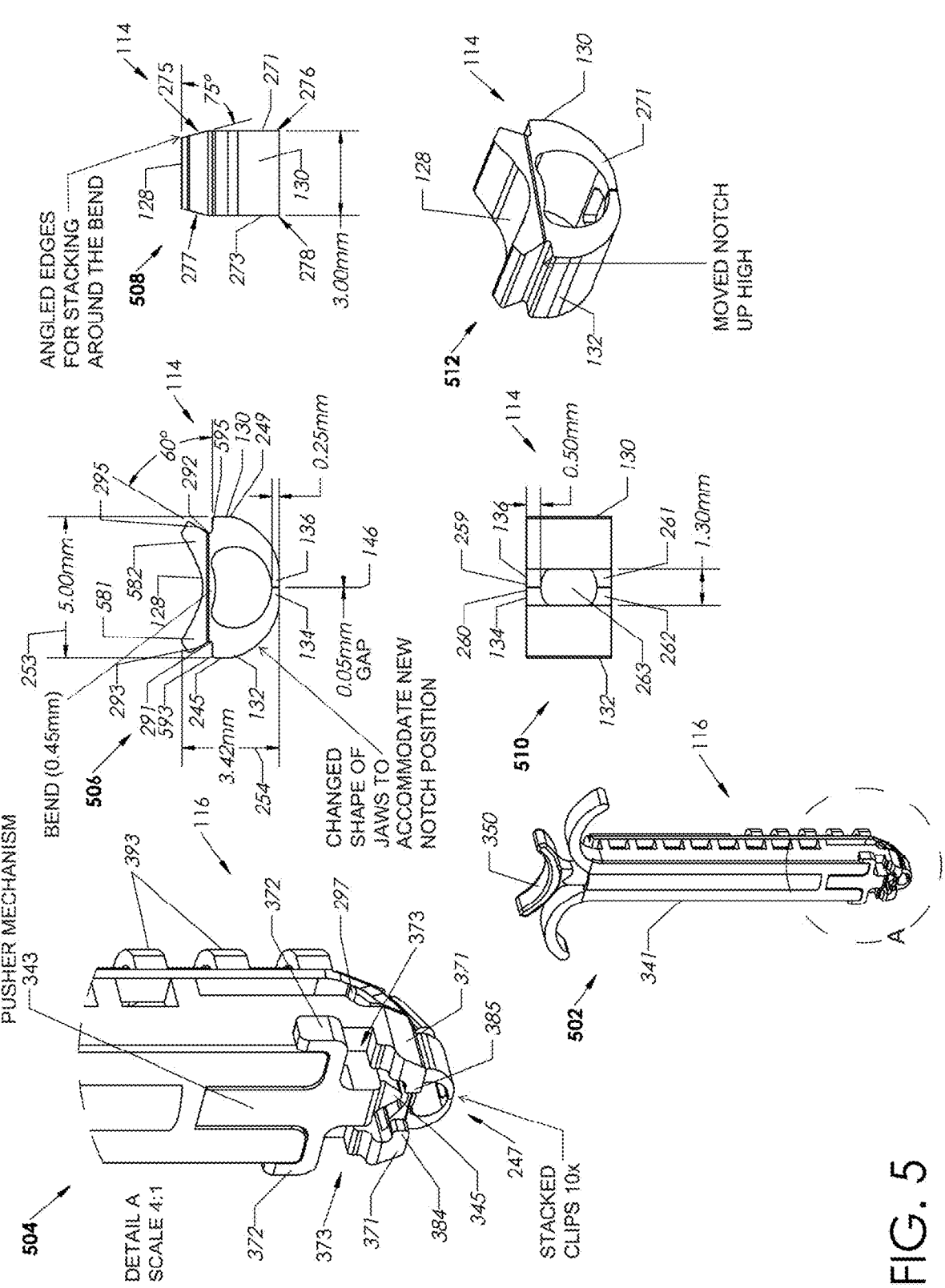
Figure 7:
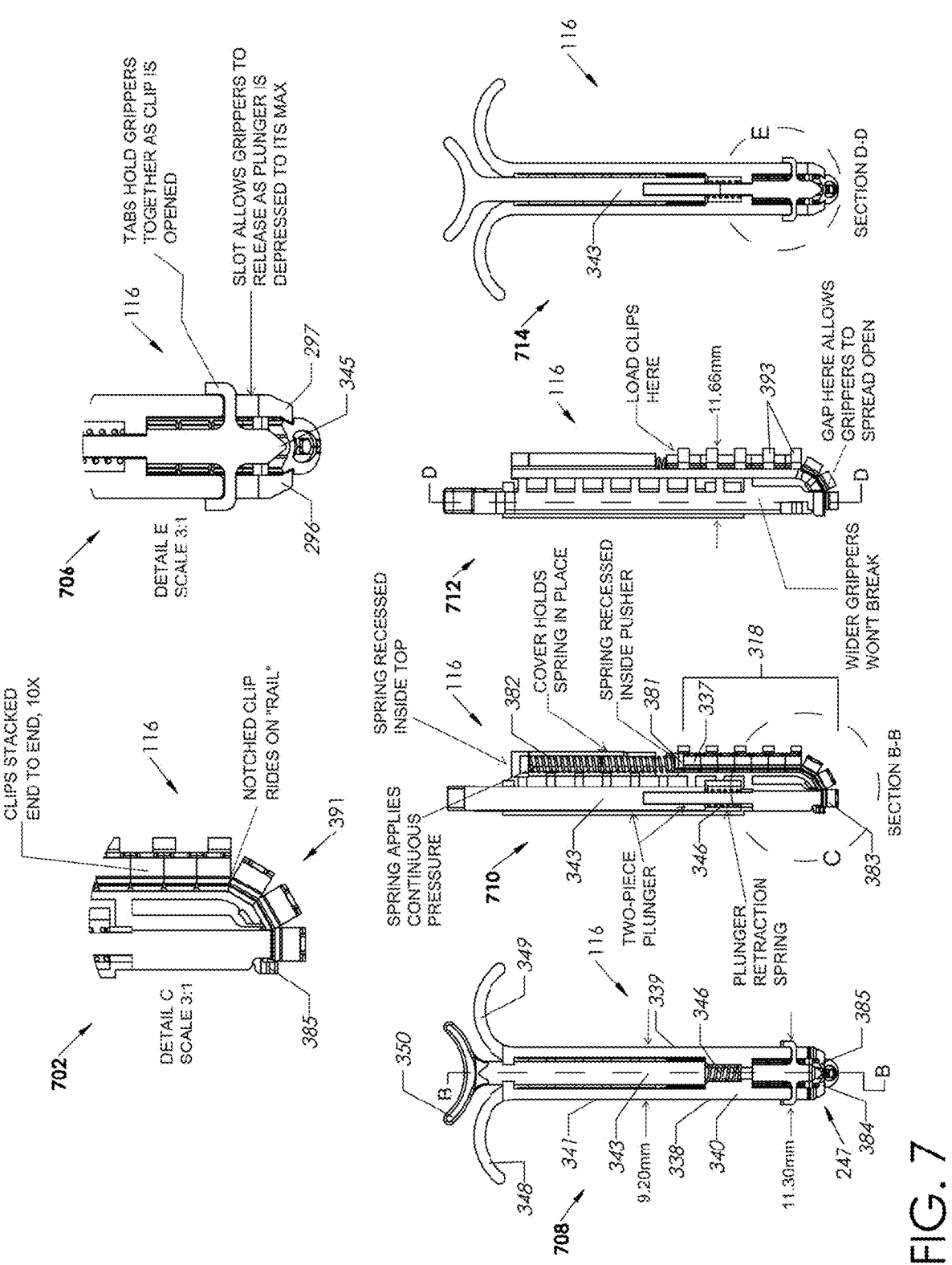

Various views and cross-sections of example surgical applicator are shown at 502, 504, 702, 706, 708, 710, 712, and 714 in FIGS. 5 and 7. In particular, at 502, a perspective view of example surgical clip applicator 116 is shown. At 504, a detailed view is shown of a distal end 247 of the applicator 116 in the region A shown in view 502. The view 504 is shown at a scale of 4:1 relative to the view shown at 502. At 708 a front view of applicator 116 is shown. At 710, a cross-section of applicator 116 is shown along section B-B shown in view 708. View 702 shows a detailed view of section C shown in view 710, where view 702 is shown at a scale of 3:1 relative to view 710. View 712 shows a side view of applicator 116. View 714 shows a cross-sectional view along cross-section D-D in view 712. View 706 shows a detailed view of region E shown in view 714 and is shown at a scale of 3:1 relative to view 714.

The surgical applicator shown in FIGS. 5 and 7 in similar to the applicator shown in FIGS. 2-3 described above. However, in this example the clip interfacing element 345 comprises a wedge-shaped component which tapers in a direction toward distal end 247. The clip interfacing element has a rounded end which can interface with the concave top portion 128 of the clip when a downward force is applied to push rod 343. Further, in this example, a spring 346 is included around a portion of the push rod at a location adjacent to the clip interfacing element 345. As remarked above, the spring 346 can comprise a wire spring encircling a portion of the push rod 343 which provides a biasing force to the push rod 343 in a direction away from the distal end 247 in order to return the push rod to an initial retracted position following an application of a downward force to the push rod via the thumb pushing element. However, in other examples, such a spring element may be omitted.

Additionally, in the example shown in FIGS. 5 and 7, the grippers 371 are held in a compressed position by opposing tabs 372 extending from the distal end of the push rod 343. Each tab in the opposing tabs 372 extends through a cut-out or aperture, e.g., apertures 373, in the arms of gripper 371 and is upwardly bent to interface with an outer surface of an arm of the gripper above the cutout to hold the grippers 371 in the compressed position so that the inwardly turned tracks hold the bottom clip 383 in place at the distal end 247 of the applicator. In particular, the tabs 372 hold the grippers 371 together for an initial duration while a downward force is applied via push rod 343 to the top portion of bottom clip 383 to open the clip. After the initial duration wherein the clip 383 is opened, application of the downward force via the push rod to the top portion of bottom clip 383 may be continued so that the tabs 272 are pushed into opposing apertures or cutouts 373 formed in opposing sides of body 341. The apertures 373 are larger than the tabs 372 so that when the tabs are moved into the apertures, constraint of the grippers by the tabs is released so that the opposing arms of the grippers move away from each other thereby releasing the clip from the distal end of the surgical applicator so that the open clip can be installed around everted tissues edges.

Figure 8:
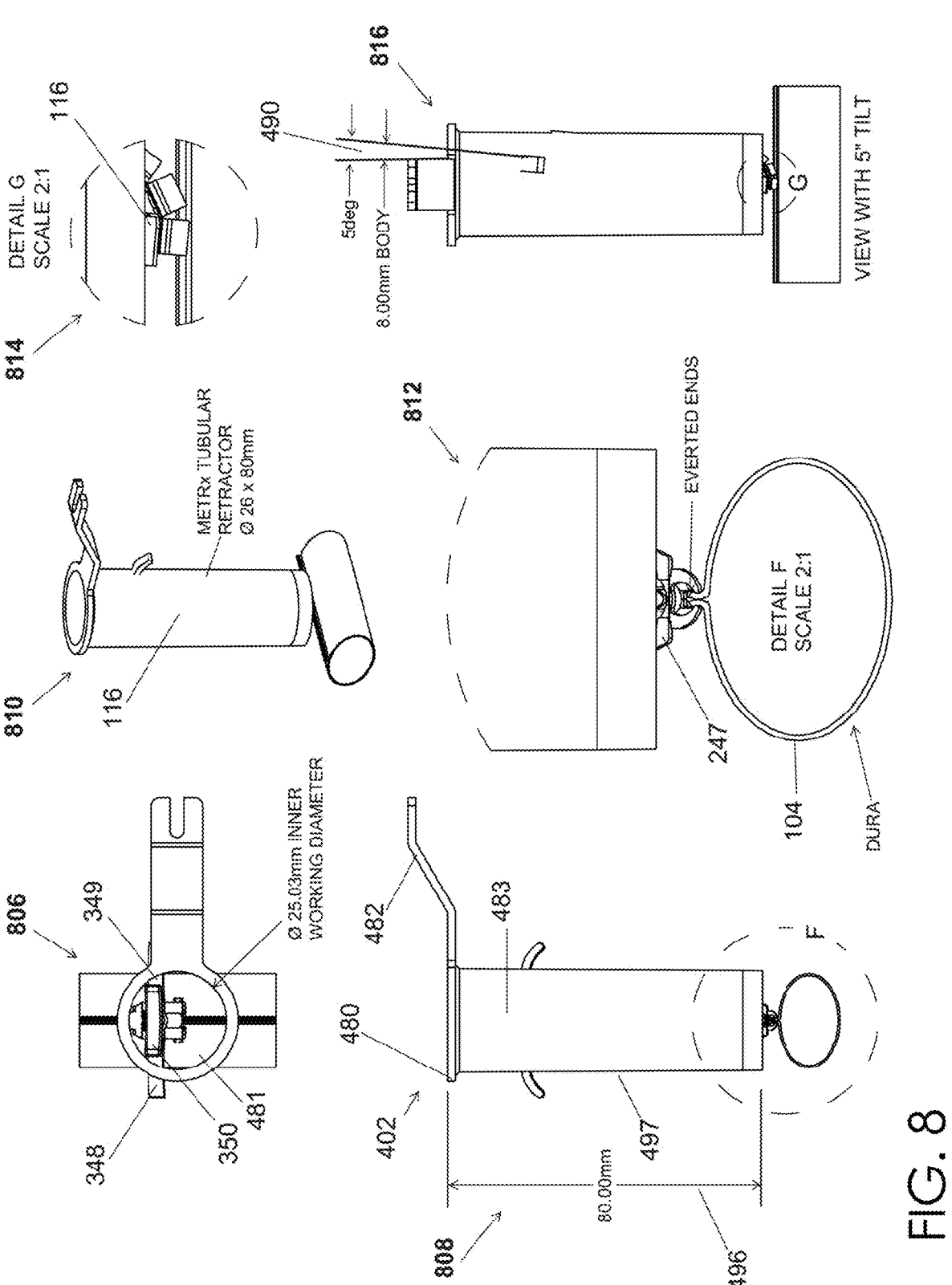

FIG. 8 shows various viewpoints and cross-sections of another example surgical clip applicator system 402 which utilizes the clip applicator and clips shown in FIGS. 5-7 described above. The embodiments shown in FIG. 8 are similar to the embodiments shown in FIG. 4 described above. In particular, at 806 a top view of the surgical clip applicator system is shown. At 808, a side view of the surgical clip applicator system is shown. At 812, a detailed view of an end of the tubular retractor 497 is shown for the region F shown in view 808. At 810, a perspective view of the surgical clip applicator system with the applicator inserted into the tubular retractor 497 at an angle is shown. At 816, a side view of the surgical clip applicator system with the applicator inserted into the tubular retractor 497 at an angle 490 is shown. View 814 shows a detailed view of the region G shown in view 816.

Figure 9:
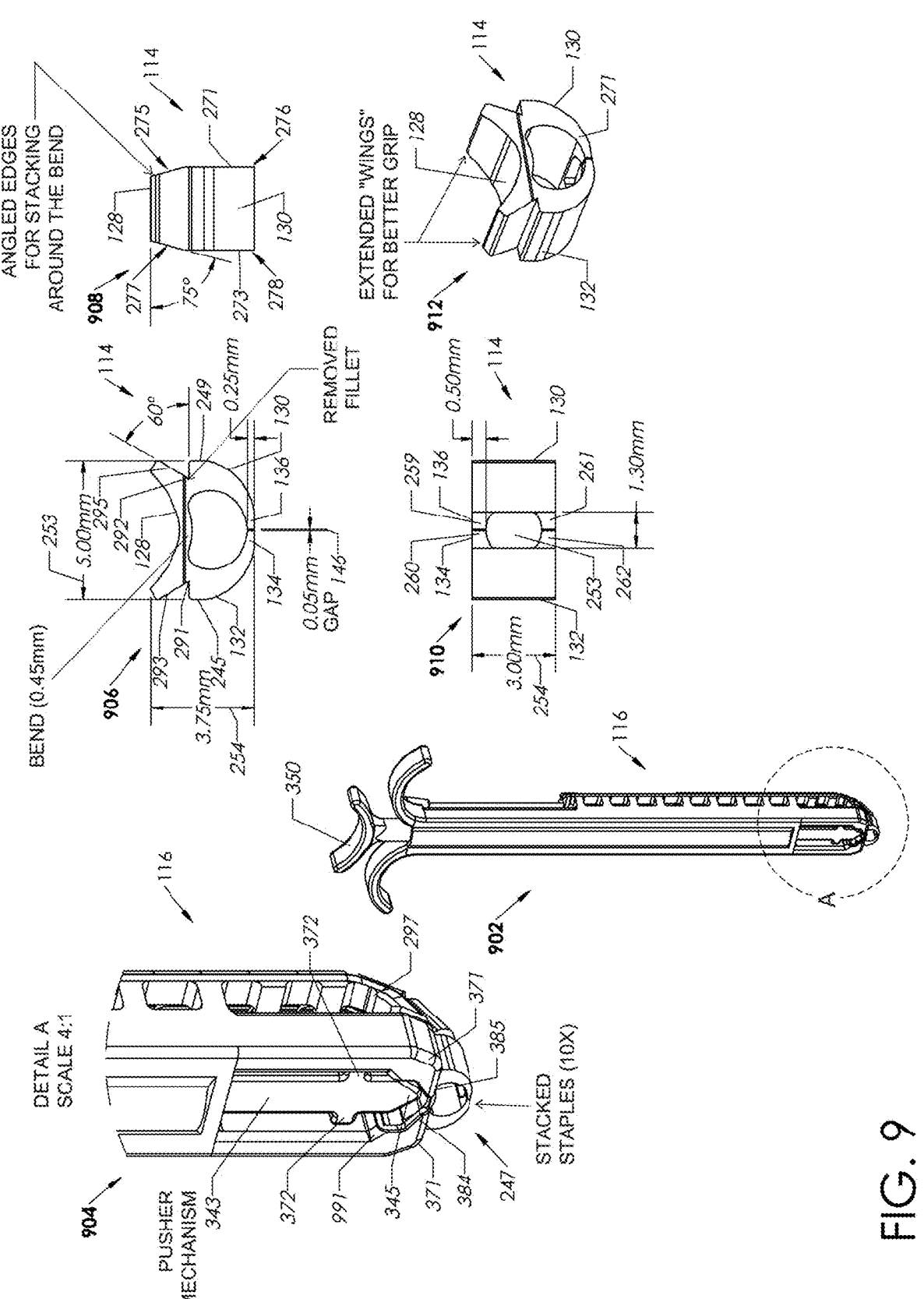
Figure 10:
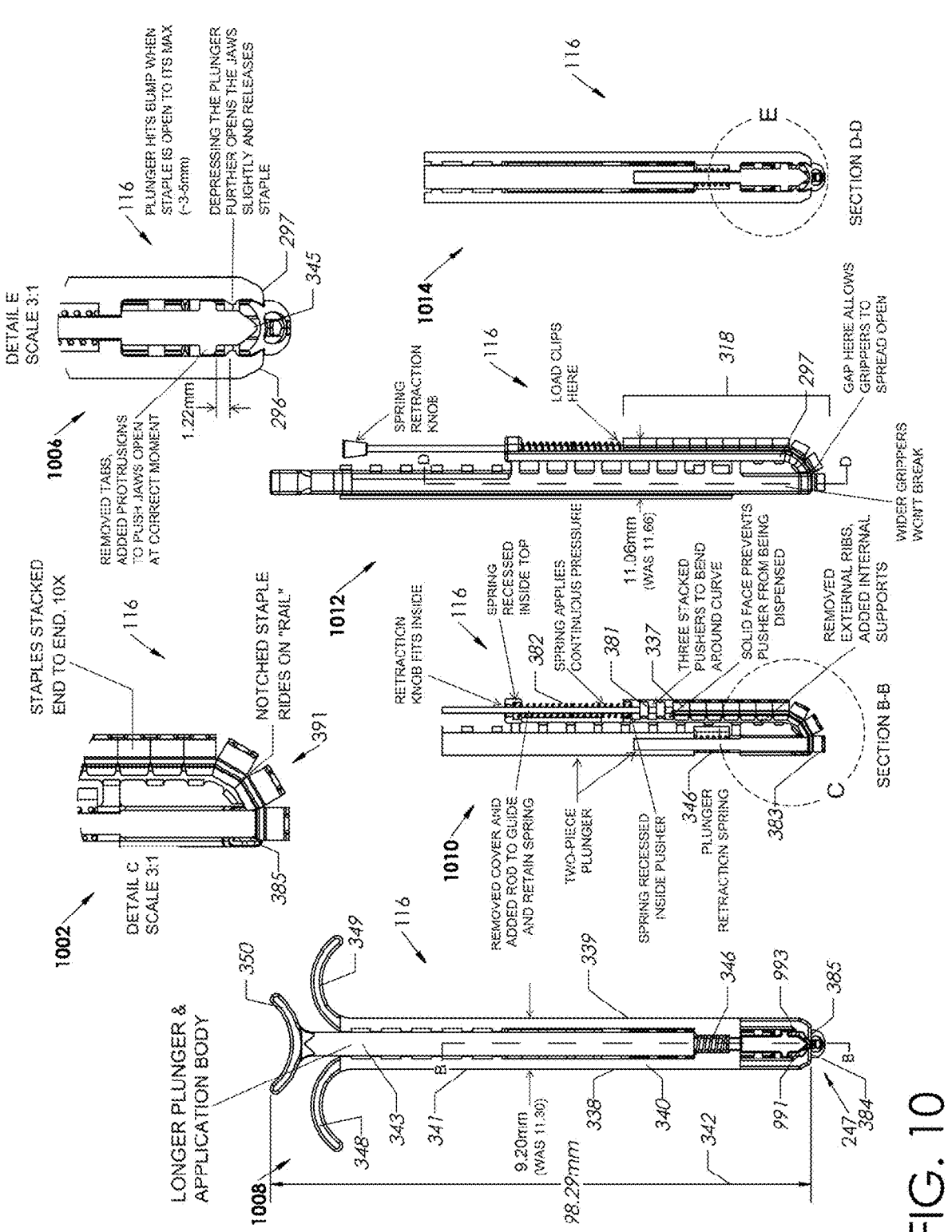

Turning to FIGS. 9-10, another example embodiment of a surgical applicator 116 and surgical clip 114 are shown from various perspectives and cross-sections. At 906, 908, 910, and 912 various viewpoints of a surgical clip 114 are shown. In particular, a front face view of an example clip 114 is shown at 906, a side view of clip 114 is shown at 908, a bottom view of clip 114 is shown at 910, and a perspective view of clip 114 is shown at 912. The surgical clip shown in FIG. 9 is similar to the surgical clip shown in FIG. 5 described above. In particular, the top portion 128 of the surgical clip comprises two opposing wings, 581 and 582, which are angled relative to each other and extend above and outward over the opposing sides 130 and 132. Further, in this example, the angled regions 275 and 277 in the faces 271 and 273 are formed in a region of the faces above the shelves 593 and 595. Additionally, in this non-limiting example, the concave top portion 128 is inwardly curved with a radius of 0.45 mm.

Various views and cross-sections of the surgical applicator are shown at 902, 904, 1002, 1006, 1008, 1010, 1012, and 1014 in FIGS. 9 and 10. In particular, at 902, a perspective view of example surgical clip applicator 116 is shown. At 904, a detailed view is shown of a distal end 247 of the applicator 116 in the region A shown in view 902. The view 904 is shown at a scale of 4:1 relative to the view shown at 902. At 1008 a front view of applicator 116 is shown. At 1010, a cross-section of applicator 116 is shown along section B-B shown in view 1008. View 1002 shows a detailed view of section C shown in view 1010, where view 1002 is shown at a scale of 3:1 relative to view 1010. View 1012 shows a side view of applicator 116. View 1014 shows a cross-sectional view along cross-section D-D in view 1012. View 1006 shows a detailed view of region E shown in view 1014 and is shown at a scale of 3:1 relative to view 1014.

The surgical applicator shown in FIGS. 9 and 10 is similar to the applicator shown in FIGS. 5 and 7 described above. However, in this example the opposing tabs 372 do not extend beyond the arms of grippers 371 but instead extend from a distal end of the push rod 343 to remain between the arms of the grippers in the interior of body 341. In this example, the grippers are formed as an extension of body 341 and remain compressed around the bottom clip to hold the clip in position at the distal end 247 of the applicator. When a downward force is applied to the push rod 343, the tabs interface with internal downwardly-angled shelves 991 and 993 to transfer outward forces to the arms of the grippers 371 so that the bottom clip is released from the inwardly turned tracks 296 and 297.

Figure 11:
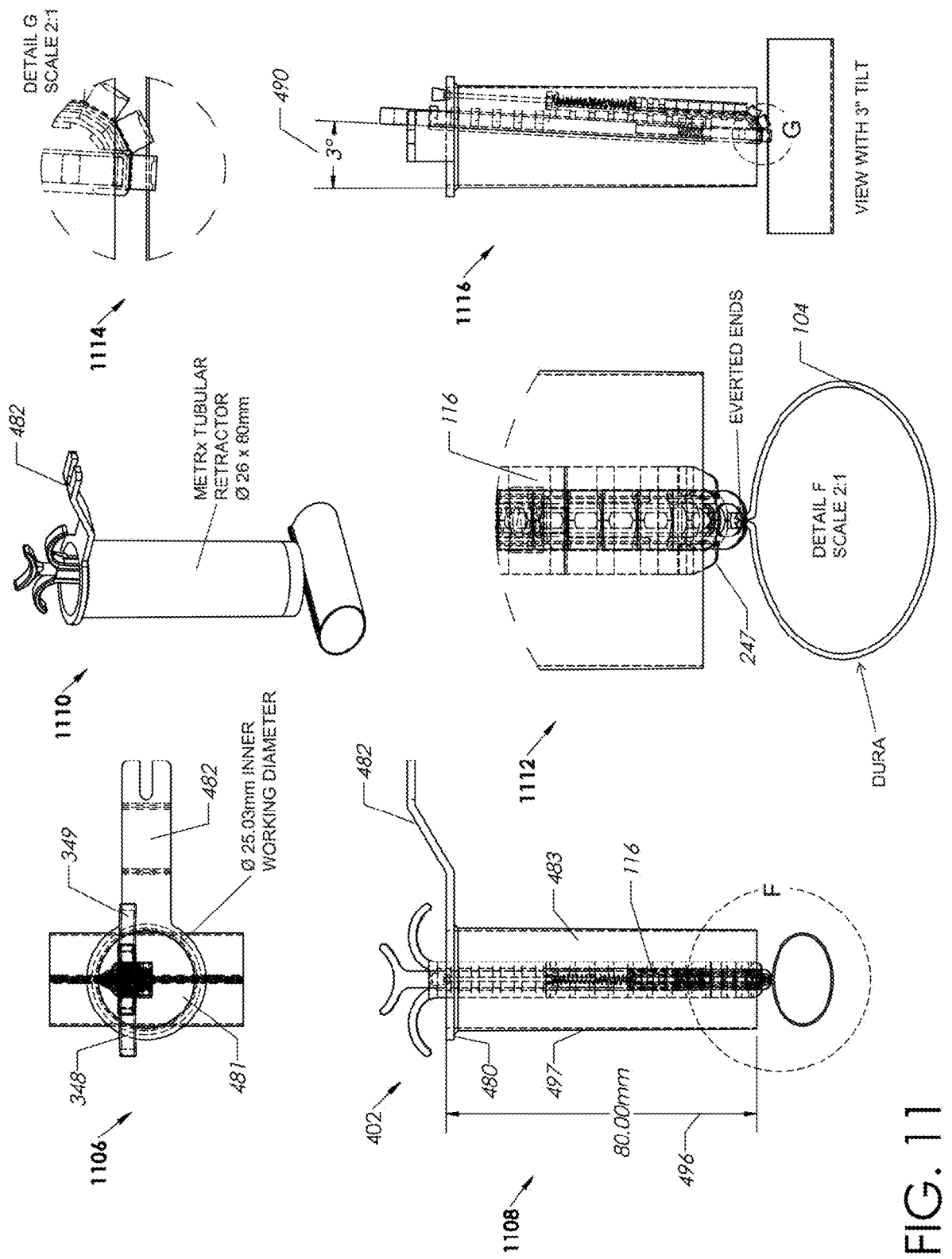

FIG. 11 shows various viewpoints and cross-sections of another example surgical clip applicator system 402 which utilizes the clip applicator and clips shown in FIGS. 9 and 10 described above. FIG. 11 is similar to FIGS. 4 and 8 described above. In particular, at 1106 a top view of the surgical clip applicator system is shown. At 1108, a side view of the surgical clip applicator system is shown. At 1112, a detailed view of an end of the tubular retractor 497 is shown for the region F shown in view 1108. At 1110, a perspective view of the surgical clip applicator system with the applicator inserted into the tubular retractor 497 at an angle is shown. At 1116, a side view of the surgical clip applicator system with the applicator inserted into the tubular retractor 497 at an angle 490 is shown. View 1114 shows a detailed view of the region G shown in view 1116.

Figure 12:
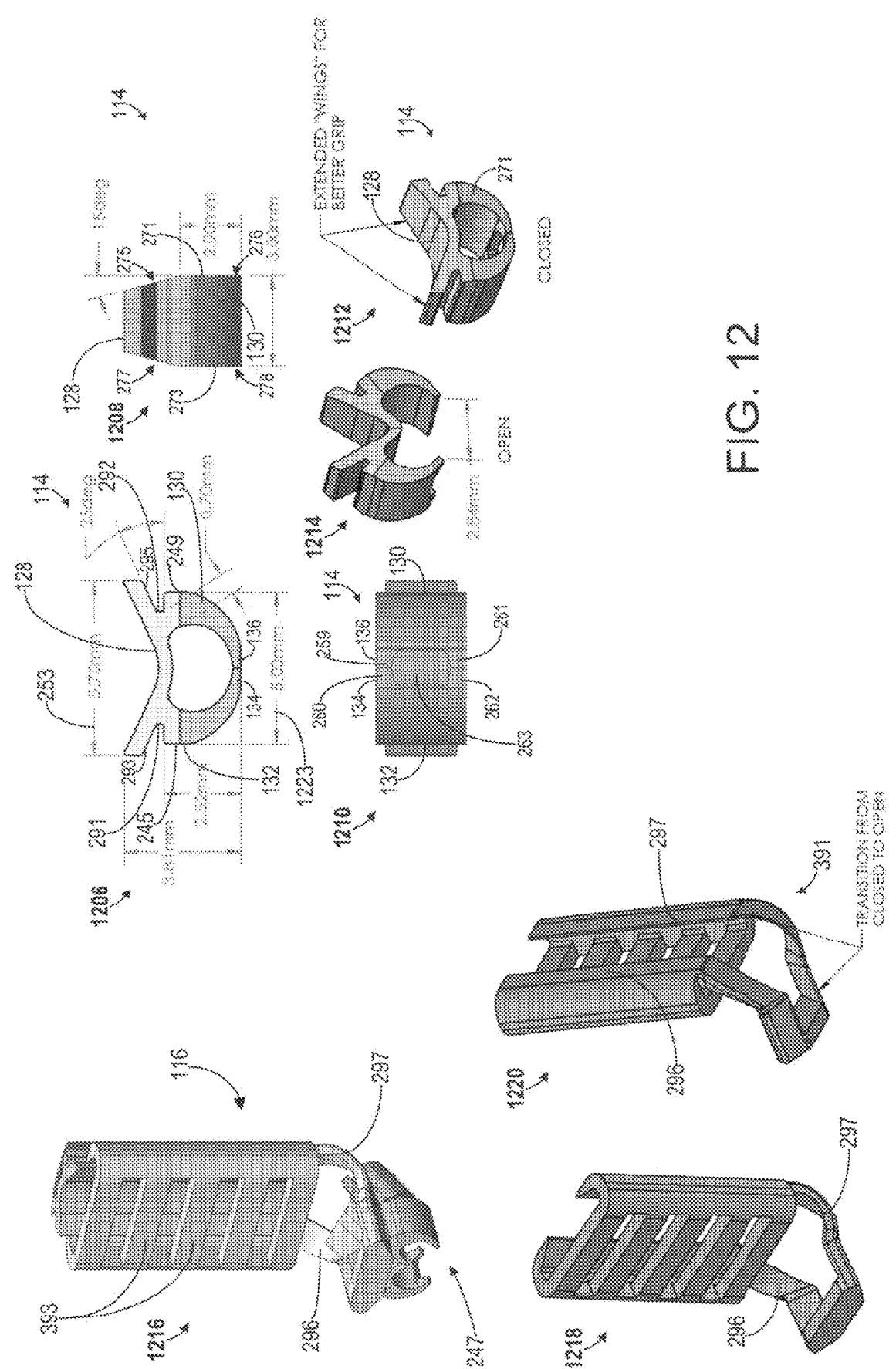

Turning to FIGS. 12-15, other example embodiments of a surgical applicator 116 and surgical clip 114 are shown from various perspectives and cross-sections. At 1206, 1208, 1210, 1212, 1306, 1308, 1310, 1312, 1314, 1316, 1318, 1320, 1322, 1324, 1406, 1408, 1410, 1412, and 1413 various viewpoints of example embodiments of a surgical clip 114 are shown. In particular, a front face view of an example clip 114 is shown at 1206, a side view of clip 114 is shown at 1208, a bottom view of clip 114 is shown at 1210, and a perspective view of clip 114 is shown at 1212. The surgical clip shown in FIG. 12 is similar to the surgical clip shown in FIG. 9 described above. However, in this example the wings 581 and 582 extend a non-zero distance beyond the sides 132 and 130 so that the length 253 of the top portion is greater than a length 1223 between the outer surface of side 132 and the outer surface of side 130. Further, in this example, the angle between the top inner surface 293 and the bottom inner surface 593 and the angle between the top inner surface 295 and the bottom inner surface 595 are both 25 degrees. Additionally, the grooves 291 and 292 in the clip shown in FIG. 12 include an inner flat region positioned between the top inner surface of the top portion, e.g., 293 and 295, and the shelves 593 and 595. Further, in this example, the angled regions 275 and 277 in the faces 271 and 273 are formed in a region of the faces extending below the shelves 593 and 595.

Figure 13:
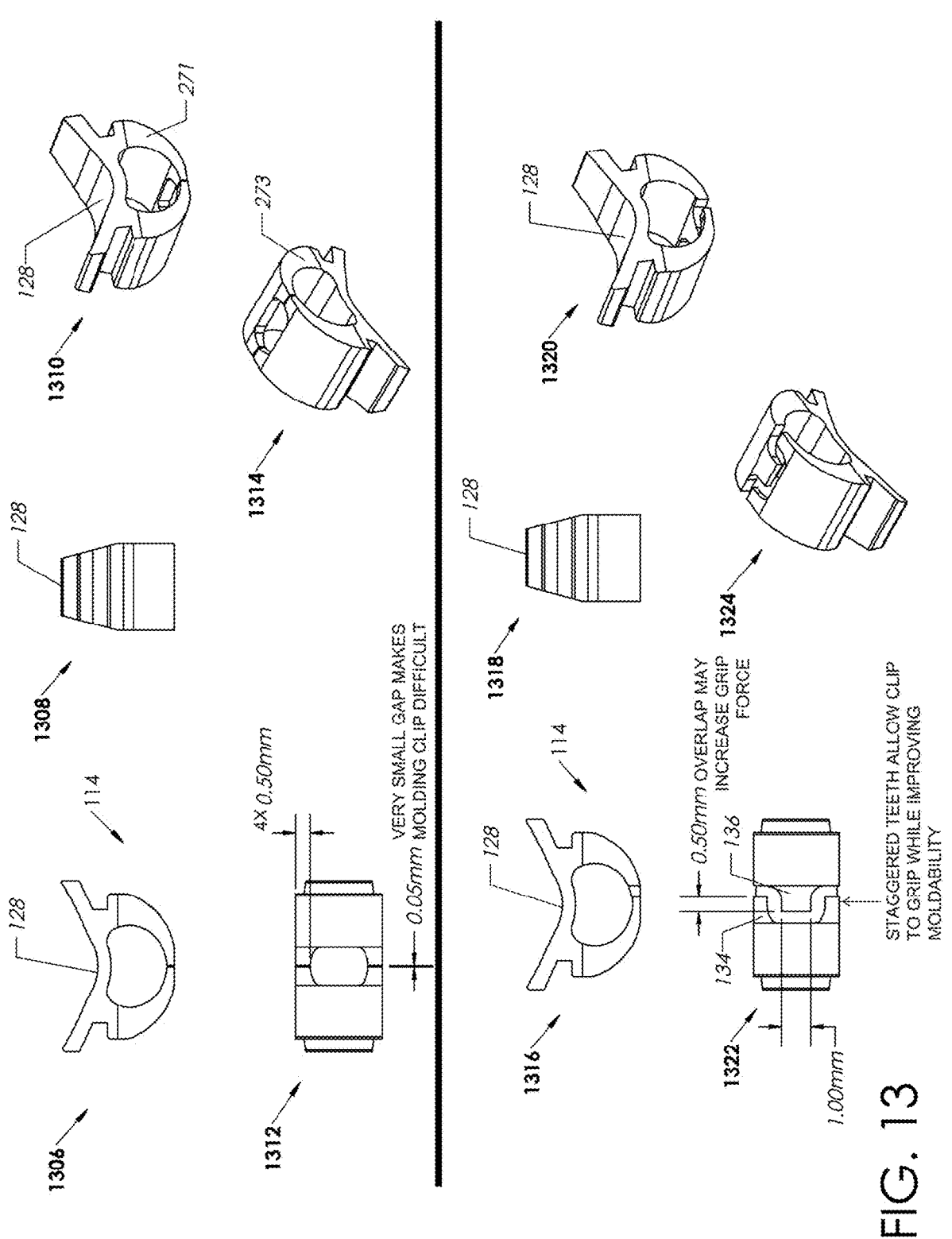
Figure 14:
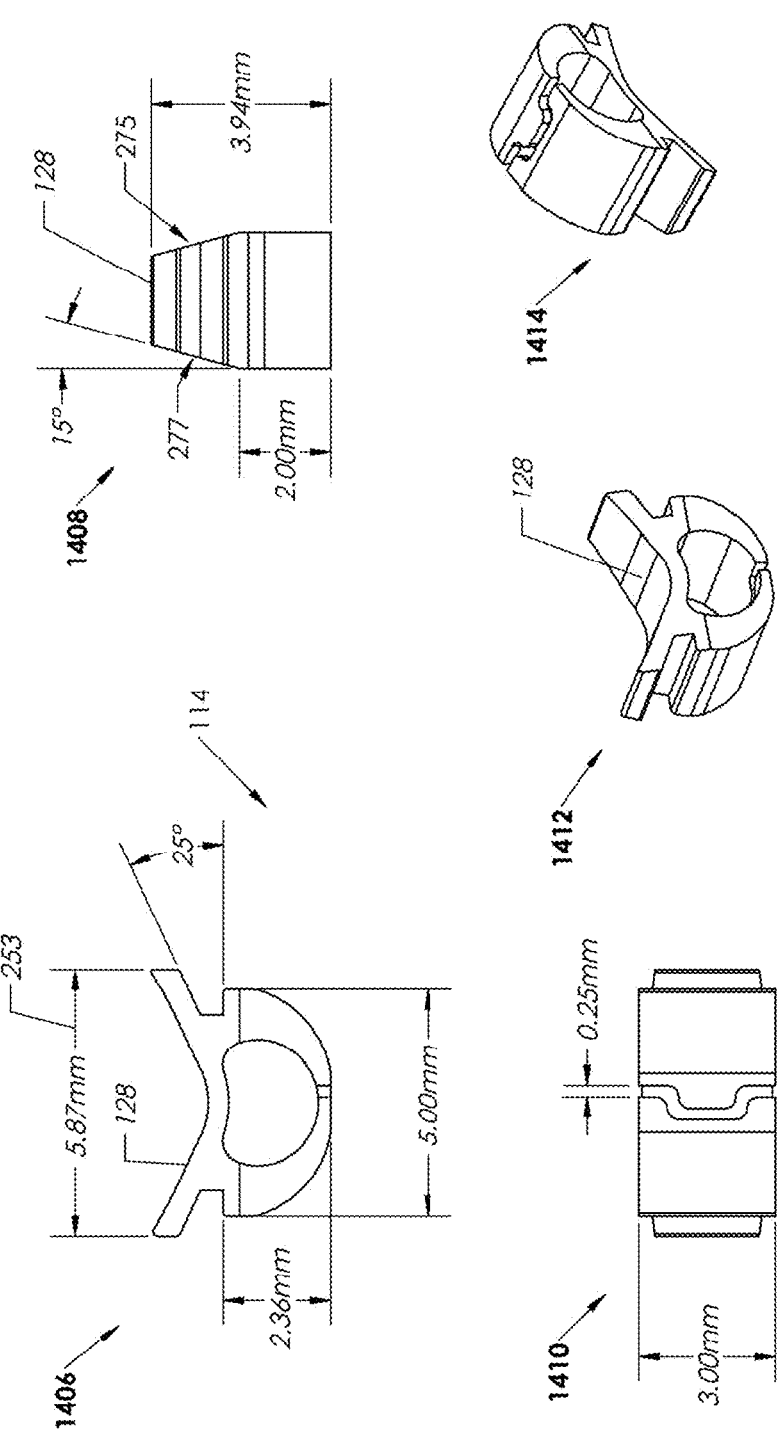

In some examples, as shown in FIGS. 13 and 14, each of the first and second tips 134 and 136 may converge to form staggered teeth. For example, tip 134 may converge in a direction towards tip 136 to form two teeth positioned adjacent to the two opposing faces and tip 136 may converge in a direction towards tip 134 to form a single tooth located between the two teeth formed by tip 134. In views 1406, 1408, and 1410 in FIG. 14, exemplary dimensions, angles, and tolerances of a surgical clip are shown in accordance with the disclosure. The dimensions shown in FIG. 14 are in millimeters.

Figure 15:
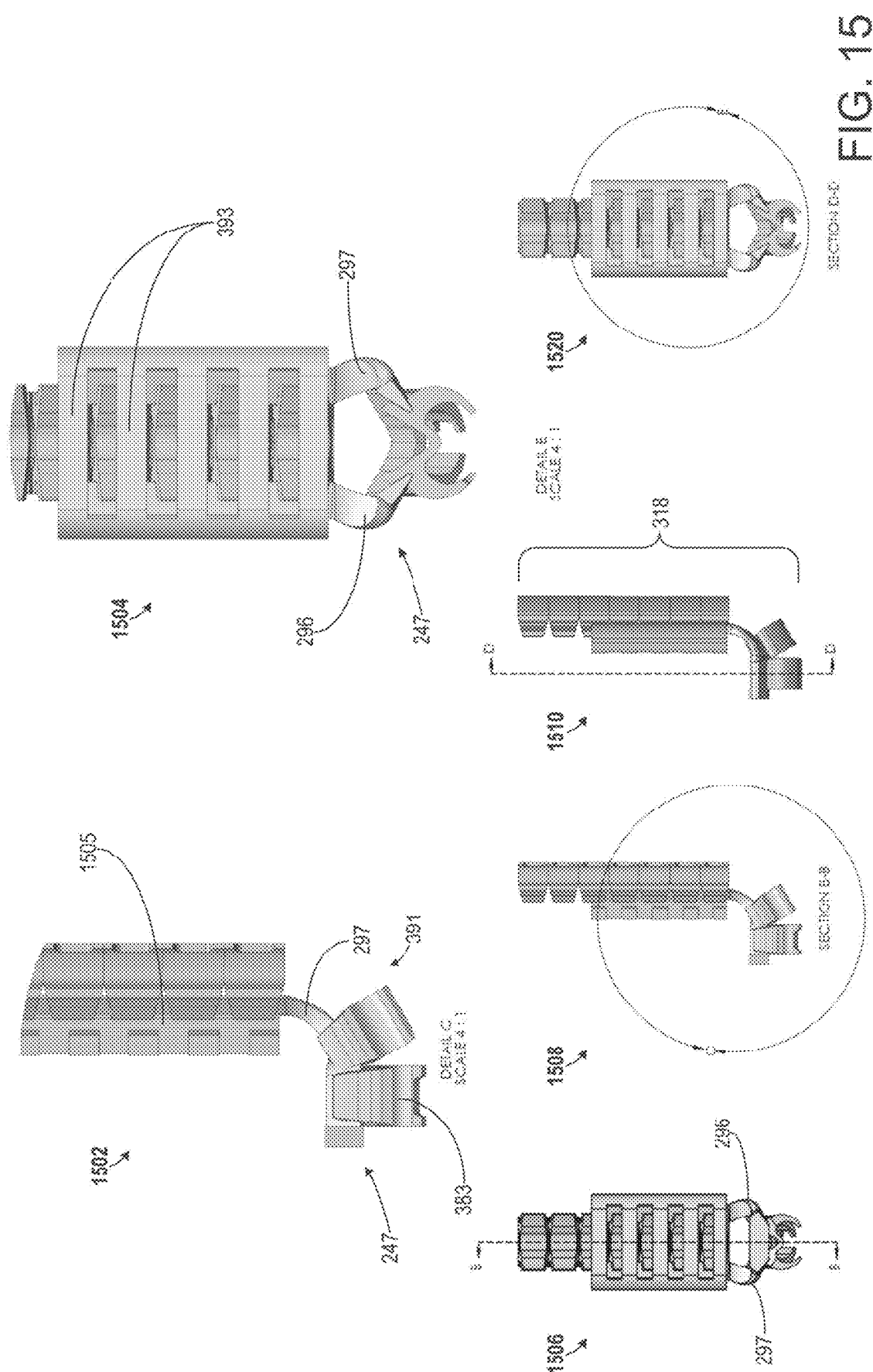

Various views and cross-sections of the fourth example surgical applicator are shown at 1216, 1218, 1220, 1502, 1504, 1506, 1508, 1510, and 1520 in FIGS. 12 and 15. In some examples, the example surgical applicator shown in FIGS. 12 and 15 may be attached adjacent to a distal end of an applicator body such as body 341 described in the examples above. In particular, the applicator shown in FIGS. 12 and 15 may include additional components, such as push rods, chambers, biasing components, etc. not shown in FIGS. 12 and 15. Views 1216, 1218, and 1220 show various perspective views of the example applicator. Views 1502, 1508, and 1510 show side views of the applicator and views 1506, 1504, and 1520 show front views of the applicator.

The surgical applicator shown in FIGS. 12 and 15 includes a chamber 1505 housing a plurality of surgical clips. The chamber 1505 has inwardly turned tracks 296 and 297 for engaging the grooves of each clip to maintain the front and back faces of each clip as orientated in the same direction as the front and back faces of the other clips in the plurality of surgical clips, yet large enough to allow movement of the plurality of clips in the direction of the faces of the clips. A direction of the inwardly turned tracks transitions from a vertical direction to a horizontal direction in a transition region 391 of the tracks. In the transition region 391, the angled regions of the faces of adjacent clips in the transition region interface with or touch each other. Additionally, a distance between the inwardly turned tracks decreases at an end of the applicator 247. In this example, the applicator includes a grating 393 in a front wall of the chamber opposing the clip array. The grating 393 extends from the transition region of the tracks in a direction away from the open end of the chamber.

Figure 16:
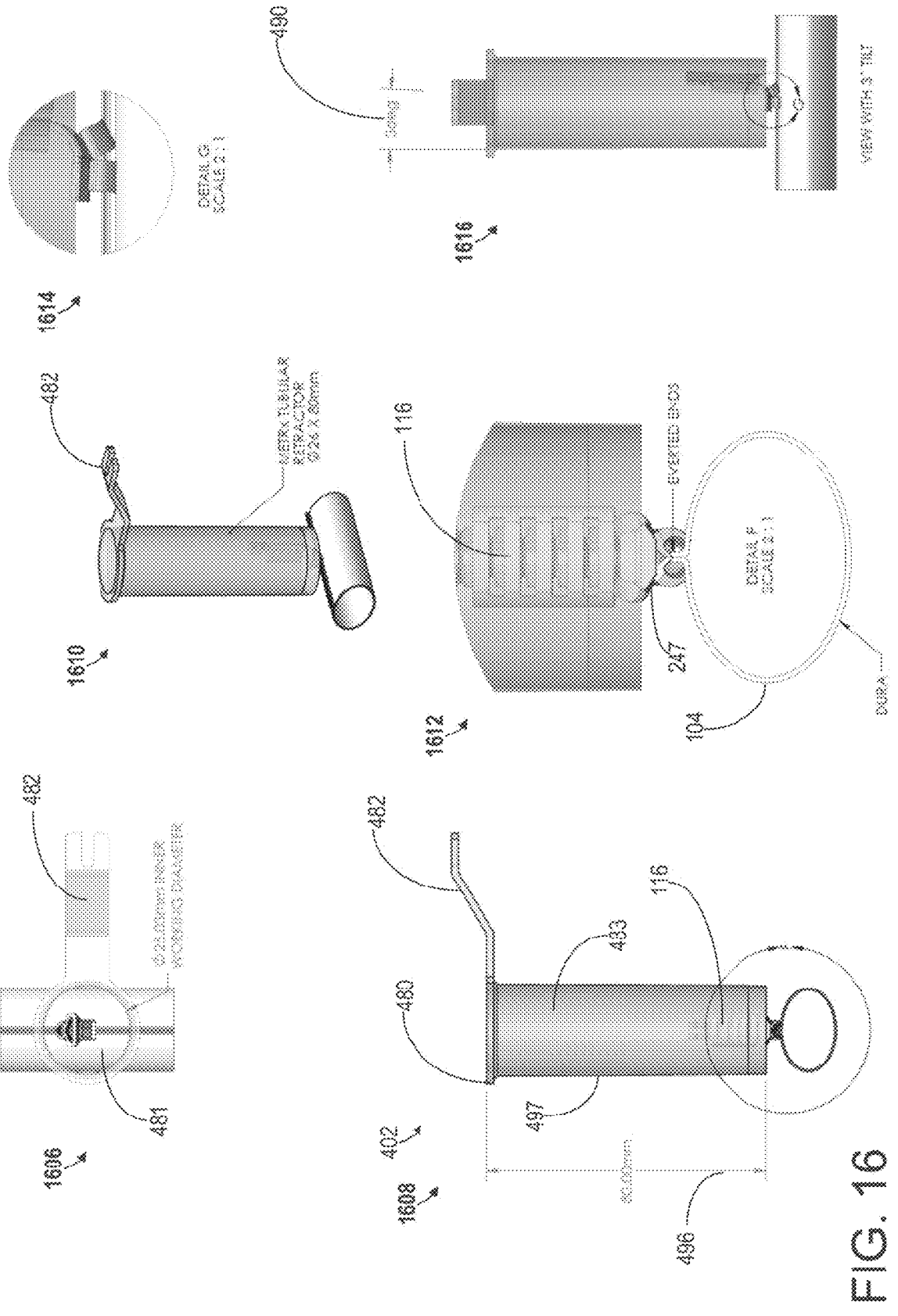
Figure 17:
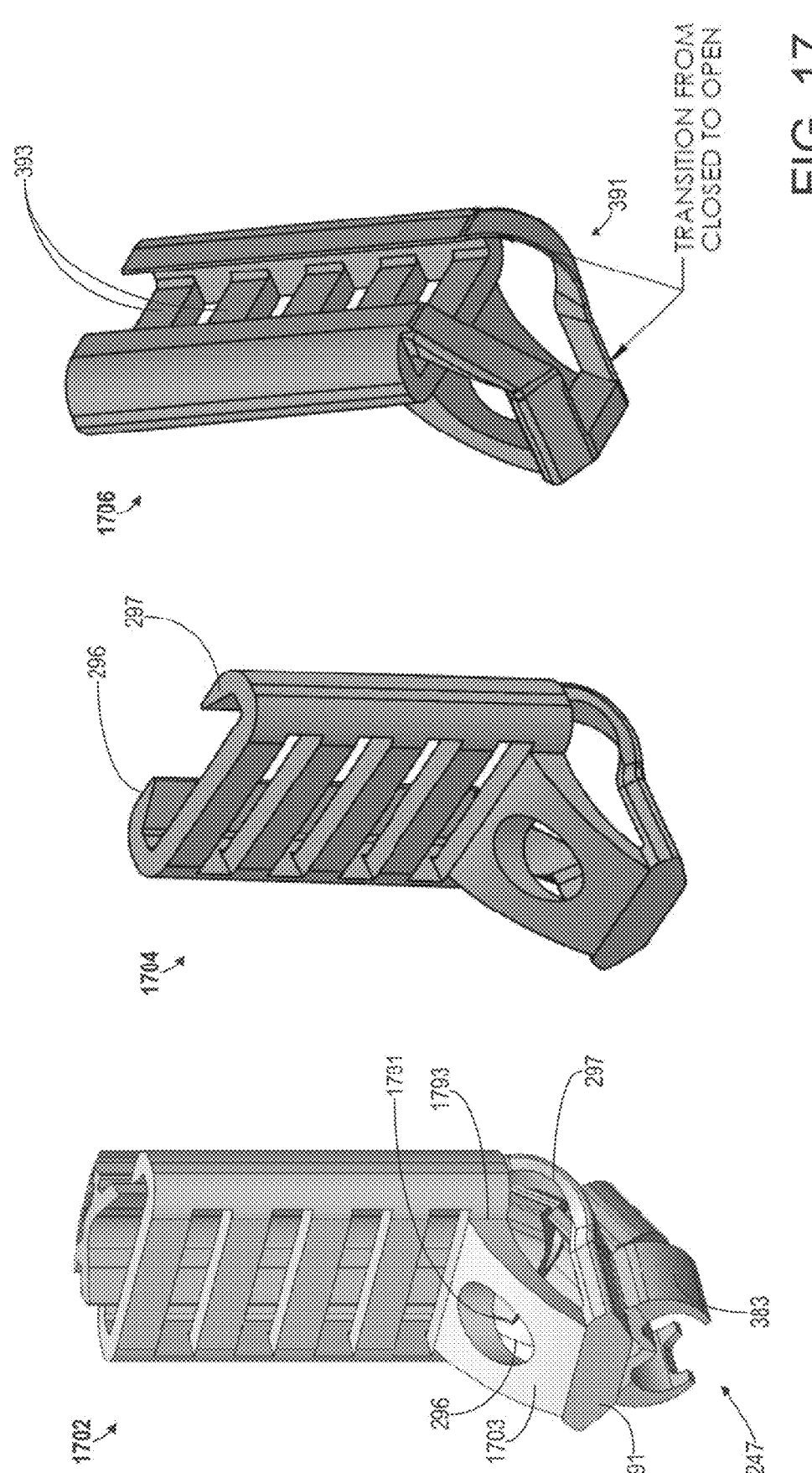
Figure 18:
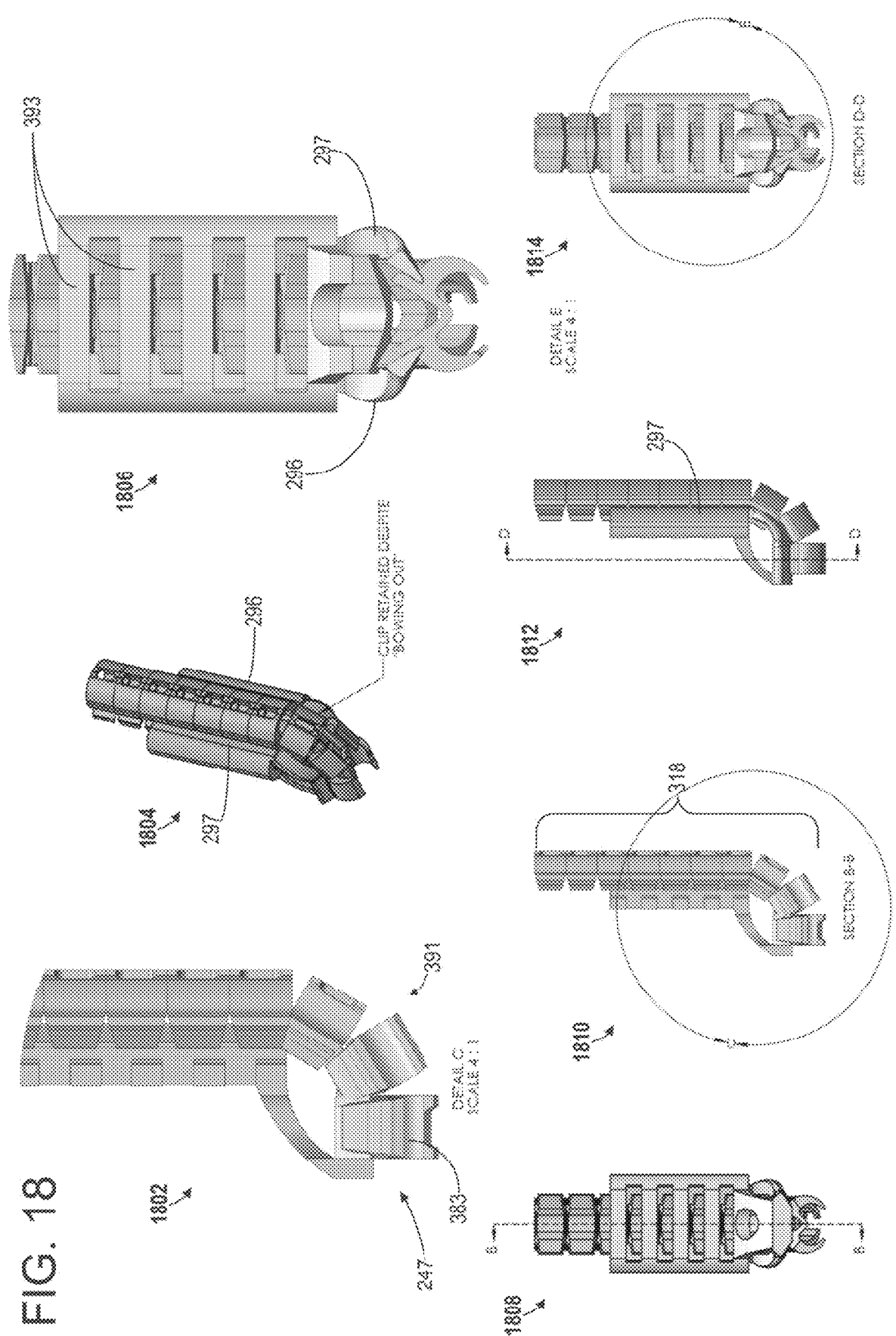
Figure 19:
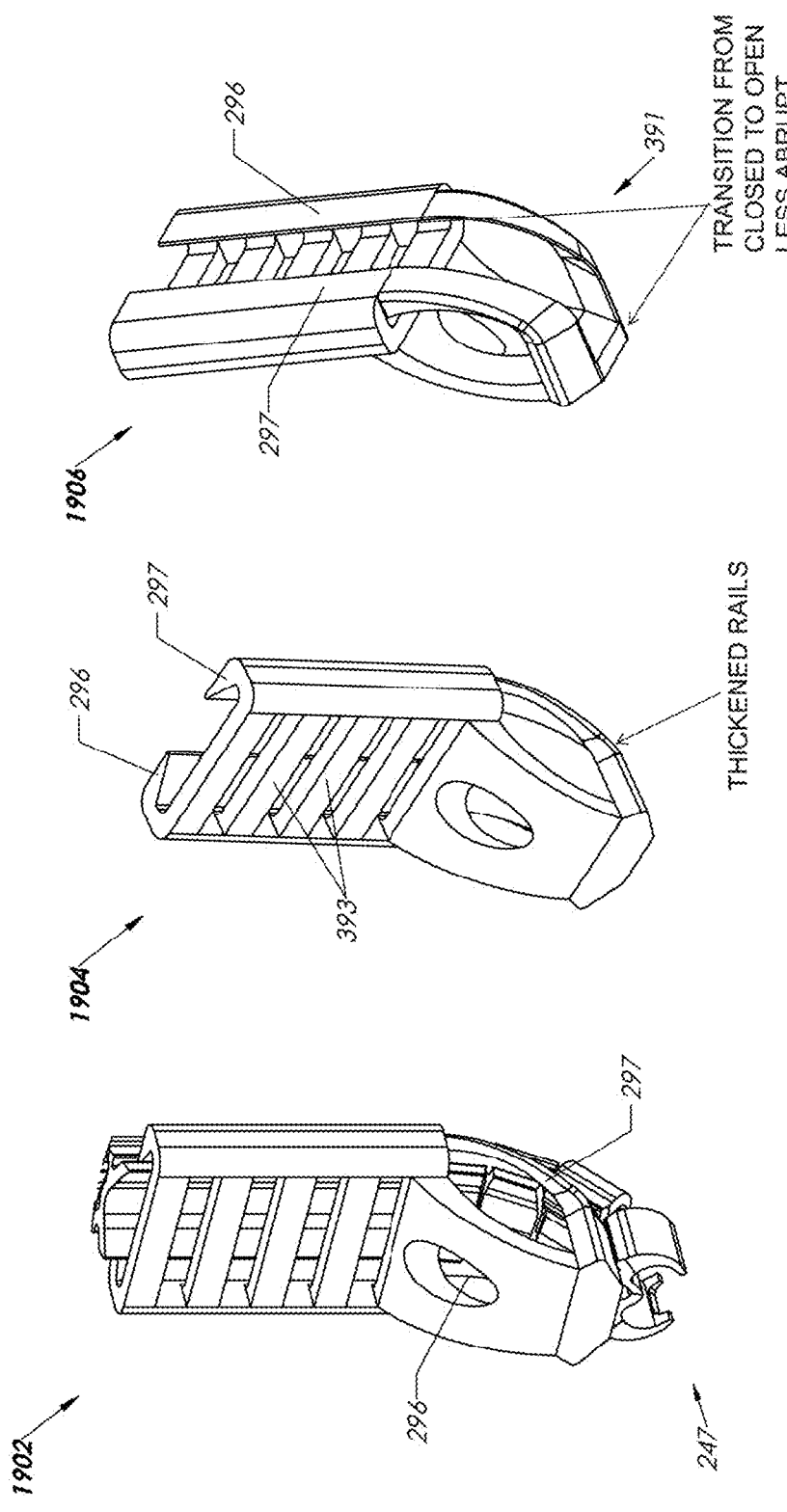
Figure 20:
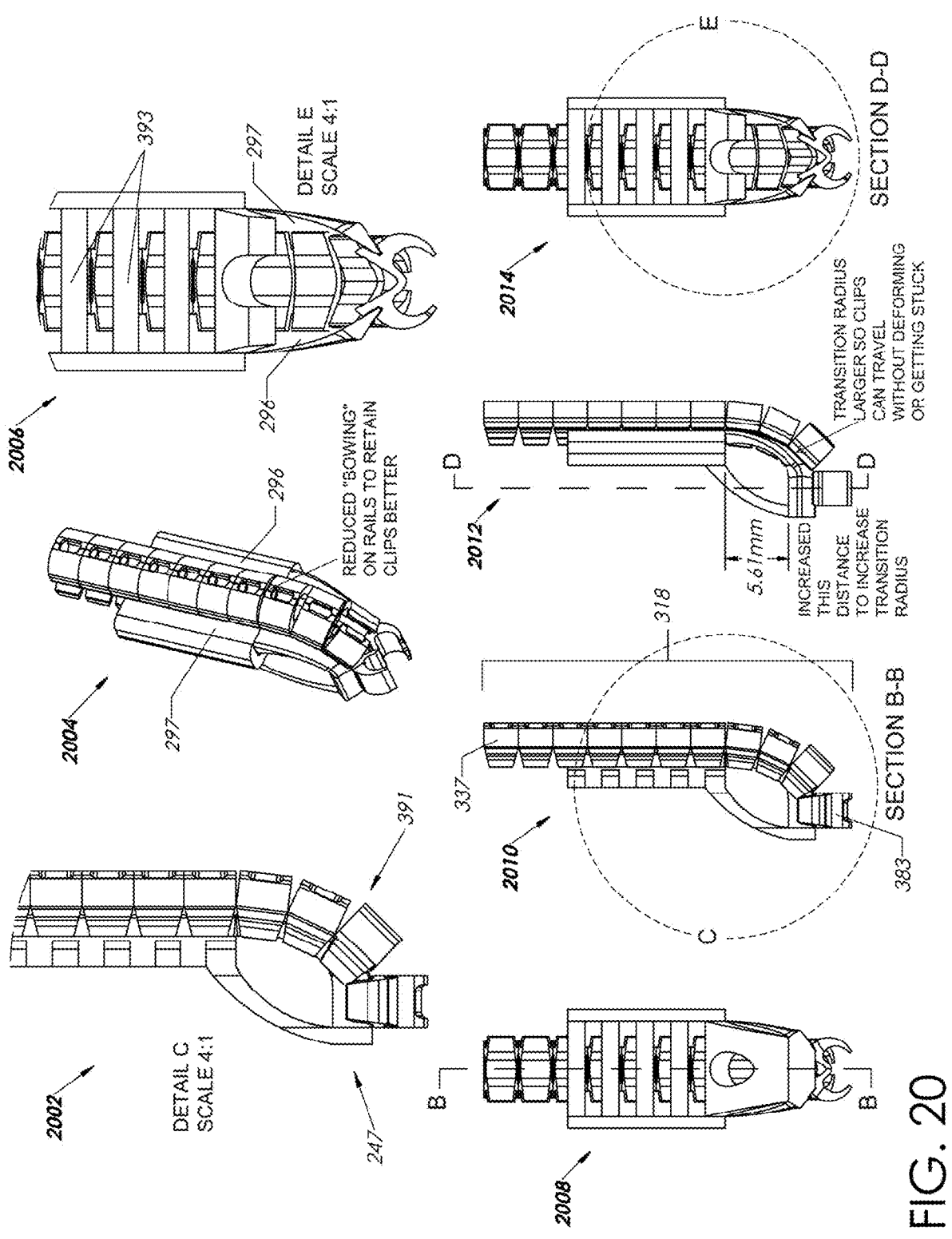

FIG. 16 shows various viewpoints and cross-sections of another example surgical clip applicator system 402 which utilizes the clip applicator and clips shown in FIGS. 12-15 described above. In particular, at 1606 a top view of the surgical clip applicator system is shown. At 1608, a side view of the surgical clip applicator system is shown. At 1612, a detailed view of an end of the tubular retractor 497 is shown for the region F shown in view 1608. At 1610, a perspective view of the surgical clip applicator system with the applicator inserted into the tubular retractor 497 at an angle is shown. At 1616, a side view of the surgical clip applicator system with the applicator inserted into the tubular retractor 497 at an angle 490 is shown. View 1614 shows a detailed view of the region G shown in view 1616.

FIGS. 17-20 show another example clip applicator which is similar to the applicator shown in FIGS. 12 and 15 described above. However, in this example, the applicator include a supporting element 1703 coupled between a bottom support member 1793 of the grating 393 and a front face 1791 of the applicator where the inwardly turned tracks, 296 and 297, terminate at the distal end 247. An aperture 1781 may be formed in the center of the supporting member 1703. For example, a push rod may be inserted through the aperture 1781 so that a force can be applied to the top portion of the bottom clip to release the clip from the applicator. The supporting member may increase stability of the applicator.

Figure 21:
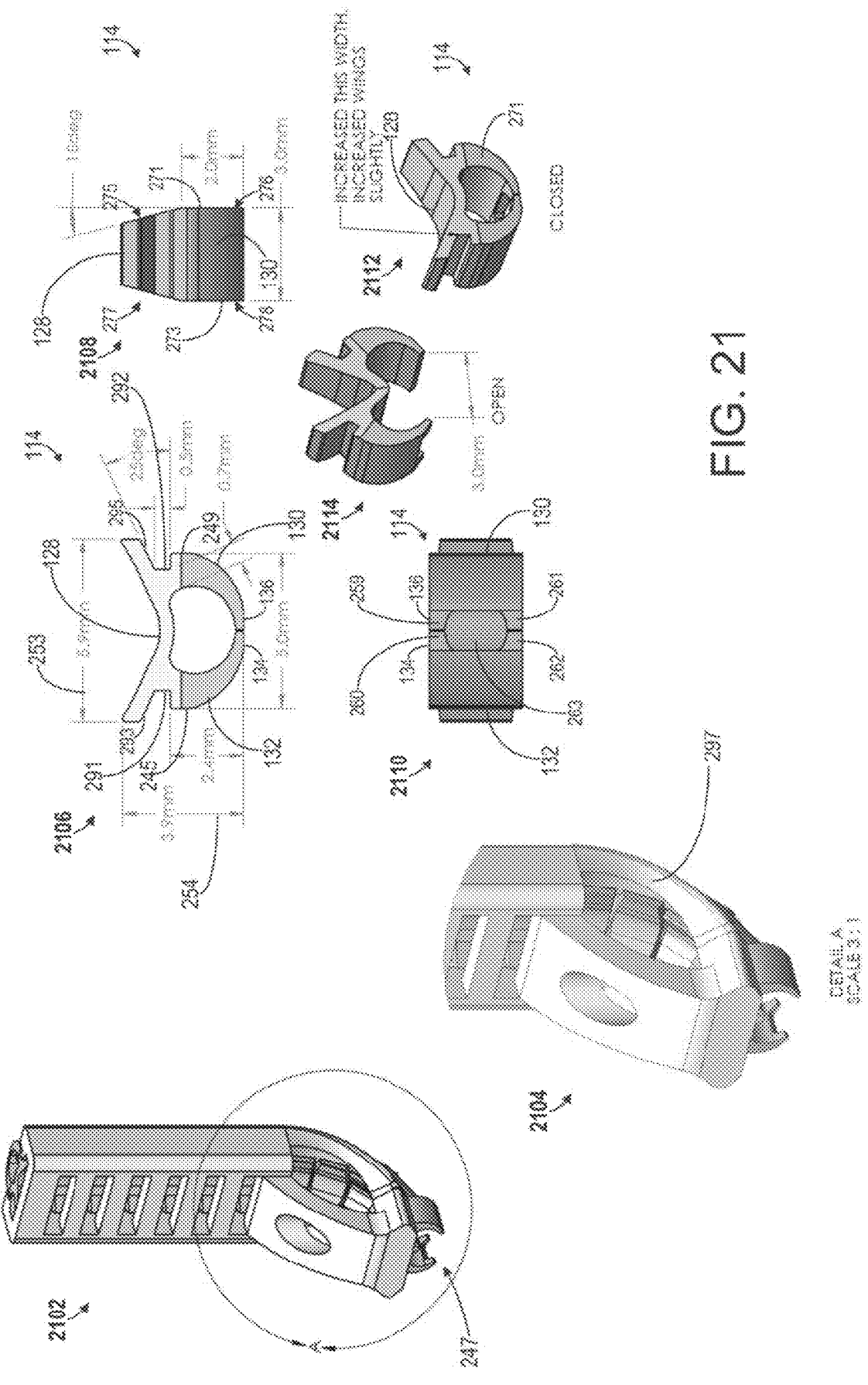
Figure 22:
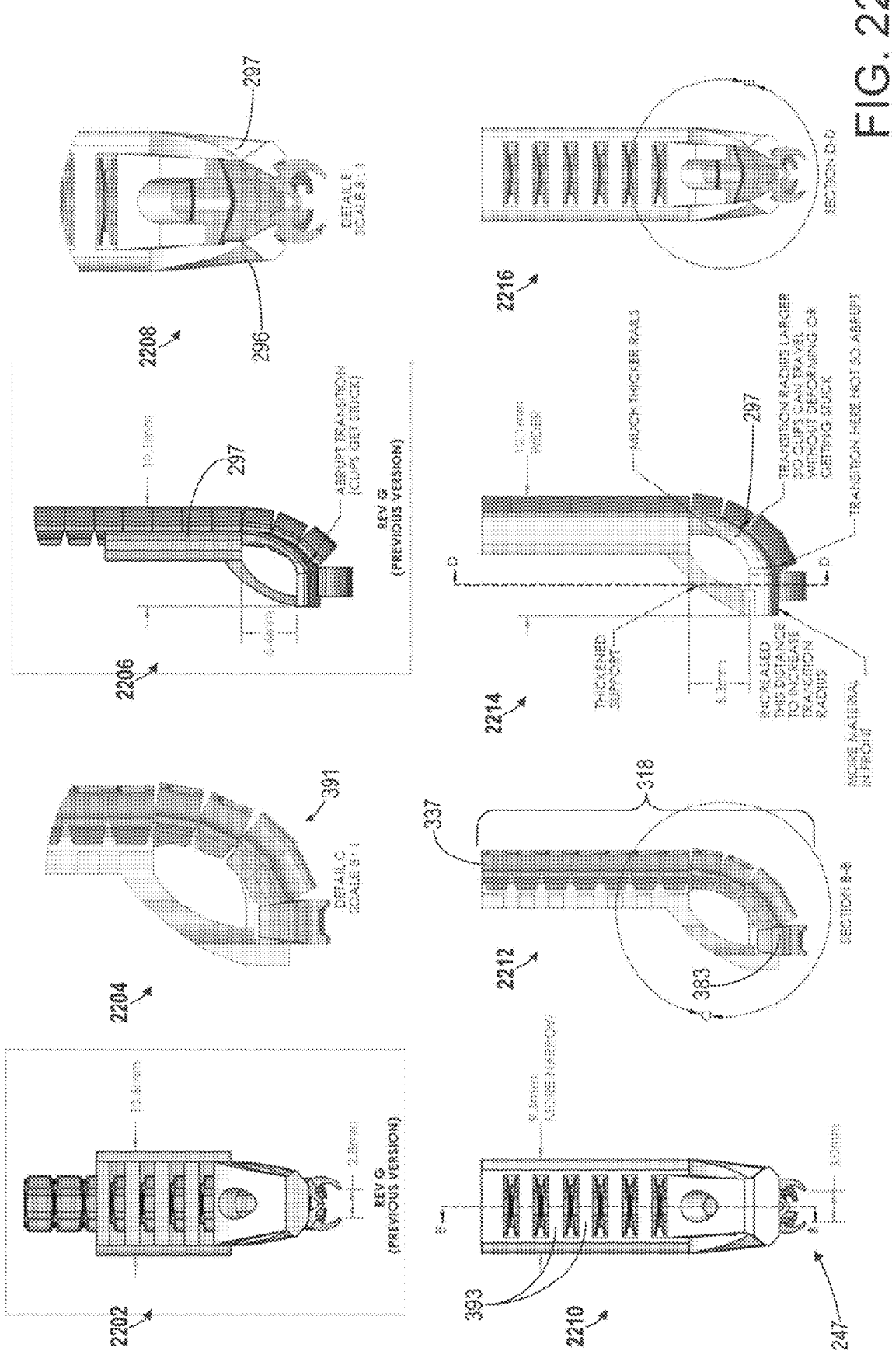
Figure 23:
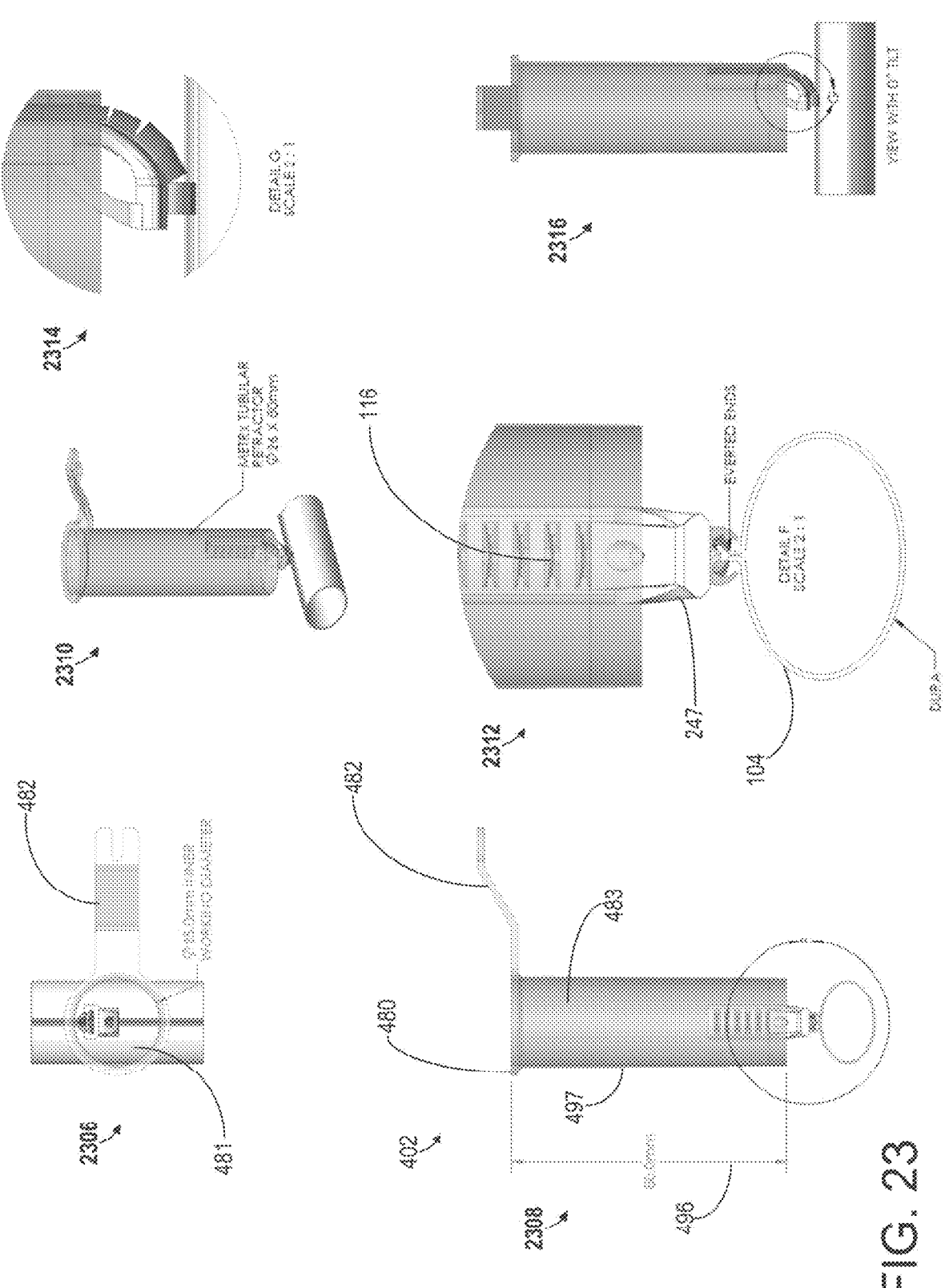

Turning to FIGS. 21-22, other example embodiments of a surgical applicator 116 and surgical clip 114 are shown from various perspectives and cross-sections. The examples shown in FIGS. 21-22 are similar to the examples shown in FIG. 12 and FIG. 17 described above. However, in this example, the transition region 391 has a greater radius to assist the movement of clips within the tracks around the transition region. FIG. 23 shows various viewpoints and cross-sections of another example surgical clip applicator system 402 which utilizes the clip applicator and clips shown in FIGS. 21 and 22 described above.

The following claims particularly point out certain combinations and subcombinations regarded as novel and non-obvious. These claims may refer to "an" element or "a first" element or the equivalent thereof. Such claims should be understood to include incorporation of one or more such elements, neither requiring nor excluding two or more such elements. Other combinations and subcombinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A surgical clip, comprising:
   first and second opposing sides extending from a top portion, wherein the first and second opposing sides terminate at first and second tips positioned below the top portion with a first distance between the first and second tips, thereby placing the clip in a closed resting position;
   wherein edges of the top portion and the first and second opposing sides form opposing front and back faces perpendicular to the first and second opposing sides, wherein the front and back faces are angled inwardly towards each other at a region of the faces adjacent to the top portion;
   a first groove formed in the first side, the first groove extending from the front face to the back face, the first groove having a top inner surface formed by a bottom surface of a region of the top portion extending over the first side;
   a second groove formed in the second side, the second groove extending from the front face to the back face, the second groove having a top inner surface formed by a bottom surface of a region of the top portion extending over the second side, where the first groove is substantially parallel to the second groove and wherein the first and second grooves are substantially perpendicular to the front and back faces at a region of the front and back faces adjacent to the first and second tips; and
   each of the first and second opposing sides comprising a flat portion coupled via an inner top junction to the top portion and coupled via a curved bottom junction to the tip.

2. The surgical clip of claim 1, wherein the first and second grooves are each configured to engage inwardly turned tracks at an end of a clip applicator such that, when a force is applied to the clip, wherein the first and second grooves are each configured to engage inwardly turned tracks at an end of said clip applicator such that when a push rod of the clip applicator is used to apply pressure to the top portion, the first and second sides bend outwardly away from each other, thereby increasing the distance between the tips to the second distance between the tips.

3. The surgical clip of claim 1, wherein the first and second grooves are each configured to engage inwardly turned tracks at an end of a clip applicator such that, when a force is applied to the clip, wherein the first and second grooves are each configured to engage inwardly turned tracks of said clip applicator, where a distance between the inwardly turned tracks decreases at an end of the clip applicator, such that when a force is applied to the back face of the clip, the clip moves within the tracks toward the end of the clip applicator thereby increasing the distance between the tips to the second distance between the tips.

4. The surgical clip of claim 1, wherein the region of the front face adjacent to the top portion is inwardly angled by approximately 15 degrees relative to the region of the front face adjacent to the first and second tips, and wherein the region of the back face adjacent to the top portion is inwardly angled by approximately 15 degrees relative to the region of the back face adjacent to the first and second tips.

5. The surgical clip of claim 1, wherein the region of the top portion extending over the first side forms two opposing wings extending a non-zero distance beyond the first and second sides so that a length of the top portion is greater than a length between an outer surface of the first side and an outer surface of the second side.

6. The surgical clip of claim 1, wherein a width of the clip is greater than at least 25% of a length of the clip, wherein the length of the clip is the dimension from the first side to the second side and the width of the clip is the dimension perpendicular to the length.

7. The surgical clip of claim 1, wherein the first tip converges in a direction toward the second tip to form two teeth positioned adjacent to the two opposing faces and the second tip converges in a direction toward the first tip to form a single tooth located between the two teeth formed by the first tip.

8. The surgical clip of claim 1, wherein the top portion is concave.

9. The surgical clip of claim 8, wherein a top surface of the top portion above the first side forms a first angle with a top surface of the top portion above the second side in the closed resting position, and wherein the top surface of the top portion above the first side forms a second angle with the top surface of the top portion above the second side in the open position, where the first angle is greater than the second angle.

10. The surgical clip of claim 1, wherein each of the first and second opposing sides is convex.

11. The surgical clip of claim 1, wherein the clip is composed of a bioabsorbable material.

12. The surgical clip of claim 1, wherein the clip is composed of a radiolucent material.

13. The surgical clip of claim 1, wherein the first and second grooves are each configured to engage inwardly turned tracks at an end of a clip applicator such that, when a force is applied to the clip, the first and second sides bend outwardly away from each other, thereby increasing the distance between the tips to a second distance between the tips.

14. A surgical clip array for a surgical clip applicator, comprising:
   a plurality of the surgical clips of claim 1;
   a chamber housing the plurality of surgical clips; and
   the chamber having inwardly turned tracks engaging the grooves of each clip to maintain the front and back faces of each clip as orientated in the same direction as the front and back faces of the other clips in the plurality of surgical clips, yet large enough to allow movement of the plurality of clips in the direction of the faces of the clips;
   wherein the plurality of clips comprises two or more clips in physical contact with one another.

15. The surgical clip array of claim 14, wherein a direction of the inwardly turned tracks transitions from a vertical direction to a horizontal direction in a transition region of the tracks and wherein the angled regions of the faces of adjacent clips in the transition region interface with each other.

16. The surgical clip array of claim 14, further comprising a top clip in the plurality of clips, wherein the back face of the top clip interfaces with a pusher element of the clip applicator.

17. A surgical clip applicator, comprising:
   a clip array of claim 14, the array comprising a chamber with an open end; and
   a push rod configured to apply pressure on a top clip in the array.

18. A surgical clip, comprising:
   first and second opposing sides extending from a top portion, wherein the first and second opposing sides terminate at first and second tips positioned below the top portion with a first distance between the first and second tips, thereby placing the clip in a closed resting position;
   wherein edges of the top portion and the first and second opposing sides form opposing front and back faces perpendicular to the first and second opposing sides, wherein the front and back faces are angled inwardly towards each other at a region of the faces adjacent to the top portion;
   a first groove formed in the first side, the first groove extending from the front face to the back face, the first groove having a top inner surface formed by a bottom surface of a region of the top portion extending over the first side;
   a second groove formed in the second side, the second groove extending from the front face to the back face, the second groove having a top inner surface formed by a bottom surface of a region of the top portion extending over the second side, where the first groove is substantially parallel to the second groove and wherein the first and second grooves are substantially perpendicular to the front and back faces at a region of the front and back faces adjacent to the first and second tips; and
   a bottom inner surface of the first groove forms an angle of approximately 25 degrees relative to the top inner surface of the first groove and wherein a bottom inner surface of the second groove forms an angle of approximately 25 degrees relative to the top inner surface of the second groove.

19. The surgical clip of claim 18, wherein an inner flat region is formed between the bottom inner surface and the top inner surface of the first groove and the inner flat region is perpendicular to the bottom inner surface of the first groove, and wherein an inner flat region is formed between the bottom inner surface and the top inner surface of the second groove and the inner flat region is perpendicular to the bottom inner surface of the second groove.

20. A surgical clip, comprising:
   first and second opposing sides extending from a top portion, wherein the first and second opposing sides terminate at first and second tips positioned below the top portion with a first distance between the first and second tips, thereby placing the clip in a closed resting position;
   wherein edges of the top portion and the first and second opposing sides form opposing front and back faces perpendicular to the first and second opposing sides, wherein the front and back faces are angled inwardly towards each other at a region of the faces adjacent to the top portion;

a first groove formed in the first side, the first groove extending from the front face to the back face, the first groove having a top inner surface formed by a bottom surface of a region of the top portion extending over the first side;

a second groove formed in the second side, the second groove extending from the front face to the back face, the second groove having a top inner surface formed by a bottom surface of a region of the top portion extending over the second side, where the first groove is substantially parallel to the second groove and wherein the first and second grooves are substantially perpendicular to the front and back faces at a region of the front and back faces adjacent to the first and second tips; and a top surface of the top portion above the first side forms a first angle with a top surface of the top portion above the second side in the closed resting position, and wherein the top surface of the top portion above the first side forms a second angle with the top surface of the top portion above the second side in the open position, where the first angle is greater than the second angle; wherein the first angle is greater than 90 degrees and the second angle is less than 90 degrees.

* * * * *